(12) United States Patent
Borrello

(10) Patent No.: US 10,821,259 B2
(45) Date of Patent: Nov. 3, 2020

(54) METHOD OF PRESSURE AND GAS MIX CONTROL FOR NON-INVASIVE VENTILATION

(71) Applicant: KONINKLIJKE PHILIPS N.V., Eindhoven (NL)

(72) Inventor: Michael Anthony Borrello, Carlsbad, CA (US)

(73) Assignee: Koninklijke Philips N.V., Eindhoven (NL)

( * ) Notice: Subject to any disclaimer, the term of this patent is extended or adjusted under 35 U.S.C. 154(b) by 240 days.

(21) Appl. No.: 15/763,901

(22) PCT Filed: Sep. 27, 2016

(86) PCT No.: PCT/IB2016/055768
§ 371 (c)(1),
(2) Date: Mar. 28, 2018

(87) PCT Pub. No.: WO2017/055995
PCT Pub. Date: Apr. 6, 2017

(65) Prior Publication Data
US 2018/0280654 A1 Oct. 4, 2018

Related U.S. Application Data

(60) Provisional application No. 62/234,089, filed on Sep. 29, 2015.

(51) Int. Cl.
*A61M 16/20* (2006.01)
*A61M 16/12* (2006.01)
*A61M 16/00* (2006.01)

(52) U.S. Cl.
CPC ...... *A61M 16/203* (2014.02); *A61M 16/0069* (2014.02); *A61M 16/026* (2017.08);
(Continued)

(58) Field of Classification Search
CPC .............. A61M 16/201; A61M 16/203; A61M 16/204; A61M 16/006; A61M 16/0069;
(Continued)

(56) References Cited

U.S. PATENT DOCUMENTS 6,131,571 A   10/2000   Lampotang et al.
7,487,773 B2 *  2/2009   Li ..................... A61M 16/0057
                                              128/204.18
(Continued)

FOREIGN PATENT DOCUMENTS

DE    102014001218 A1   7/2015
EP         2425869 A1   3/2012
(Continued)

*Primary Examiner* — Samchuan C Yao
*Assistant Examiner* — Margaret M Luarca
(74) *Attorney, Agent, or Firm* — Daniel H. Brean

(57) ABSTRACT

A ventilator (100) configured to control a pressure and gas mixture for an air flow. The ventilator include: a gas source (220); a proportional valve (210) configured to control a gas flow rate from the gas source; a mix controller (170) in communication with the proportional valve, the mix controller configured to monitor a flow of gas through the blower, and further configured to control a percentage of oxygen in the output flow; a blower motor (160); and a blower motor controller (162) configured to control a speed of the blower motor using a current feedback loop, a blower speed feedback loop, a flow feedback loop, and a pressure feedback loop. The ventilator can also include, for example, a pseudo-derivative feedback compensator, a complimentary filter, and/or a speed controller.

10 Claims, 11 Drawing Sheets

(52) U.S. Cl.
CPC ............ *A61M 16/12* (2013.01); *A61M 16/125* (2014.02); *A61M 16/204* (2014.02); *A61M 2016/0033* (2013.01); *A61M 2202/0208* (2013.01); *A61M 2205/50* (2013.01); *A61M 2205/75* (2013.01)

(58) Field of Classification Search
CPC ............ A61M 16/022; A61M 16/0057; A61M 16/066; A61M 16/024
See application file for complete search history.

(56) References Cited

U.S. PATENT DOCUMENTS

| | | |
|---|---|---|
| 8,794,234 B2 | 8/2014 | Jafari et al. |
| 2007/0175473 A1 | 8/2007 | Lewis et al. |
| 2010/0319697 A1* | 12/2010 | Farrugia ............... F04D 27/001 128/204.18 |
| 2012/0006326 A1 | 1/2012 | Ahmad |
| 2012/0157794 A1 | 6/2012 | Goodwin et al. |
| 2013/0228180 A1* | 9/2013 | Ahmad ............. A61M 16/0069 128/204.23 |
| 2015/0000663 A1 | 1/2015 | Williams et al. |

FOREIGN PATENT DOCUMENTS

| | | |
|---|---|---|
| WO | 9809677 A1 | 3/1998 |
| WO | 2005016217 A2 | 2/2005 |
| WO | 2012032434 A1 | 3/2012 |

\* cited by examiner

METHOD OF PRESSURE AND GAS MIX CONTROL FOR NON-INVASIVE VENTILATION

CROSS-REFERENCE TO PRIOR APPLICATIONS

This application is the U.S. National Phase application under 35 U.S.C. § 371 of International Application No. PCT/IB2016/055768, filed on Sep. 27, 2016, which claims the benefit of U.S. Provisional Patent Application No. 62/234,089, filed on Sep. 29, 2015. These applications are hereby incorporated by reference herein.

FIELD OF THE INVENTION

The present disclosure is directed generally to methods and systems for precisely controlling pressure and gas mix in a ventilator system.

BACKGROUND

The most common means of providing critical care ventilation requires intubating patients with an endotracheal tube that seals within the trachea using an inflatable cuff. Intubation offers the best means of clinically managing the airway and maintaining lung inflation, but it introduce significant risks including tissue abrasion, infection, and sedation of the patient due to extreme discomfort. Accordingly, intubation is appropriately called invasive ventilation, and the clinician's decision to intubate must be carefully considered. For a select group of hospitalized patients requiring breathing support, the risks leading to adverse side effects of intubation can outweigh the benefits.

In light of significant risks of invasive ventilation, an alternative approach was developed from home care ventilation that offers the benefit of applying support through the airway, however using a connection by means of a mask over the patient's mouth and nose, or a tracheostomy tube. This approach is called non-invasive positive pressure ventilation, or simply non-invasive ventilation (MV). For non-invasive ventilation, some leak is expected and often purposely introduced in order to reduce end-tidal $CO_2$ that would otherwise be rebreathed by the patient, since a single limb circuit connects the ventilator to the mask in a non-invasive ventilation system. In comparison, invasive ventilation uses a dual-limb connecting circuit that separately carries exhaled gases, which prevents rebreathing of $CO_2$ in invasive ventilation which therefore requires no leak.

Non-invasive ventilation of critical care patients typically uses a combination of a blower as an ambient air source and a proportional valve as a source for compressed oxygen, in order to control pressure and gas mix (i.e., the percentage oxygen concentration) during breath delivery. In some designs, the proportional valve introduces pure oxygen into the low pressure or inlet side of a blower such that the blower flow control entirely generates pressure for breath delivery whereas in other designs the proportional valve introduces gas into the high pressure side, or outlet, of the blower. In the latter case, both the blower and proportional valve generate pressure. However, coordinating the blower and proportional valve controls to achieve precise and accurate pressure and mix presents multiple problems. For example, the blower flow response time is typically much slower than the response time of the valve since the blower inertia requires time to accelerate. The slow response of the blower itself affects the pressure response time in general, but the flow-dynamic mismatch between blower and valve makes pressure and mix controls a challenging problem. Additionally, although a proximal pressure sense line is provided in non-invasive ventilation, using that pressure as the source for control introduces significant delay in the feedback loop. Directly closing the loop between measured proximal pressure, while affording more accurate steady state pressure at the patient's airway, limits the speed at which pressure changes can be made due to stability. While a blower speed loop might help to improve response, at low flow there is low speed and Hall sensing tachometer readings drop out. Encoder controlled speed can be used, but that decreases blower system reliability and increases cost.

Current systems also have difficulty dealing with the effects of disturbance, which must be taken into account as part of the design in order to ensure that the controls follow the desired target pressure in spite of the disturbance, and that the controls attenuate rather than amplify disturbance. Sources of non-invasive ventilation disturbances include, for example: (a) flow disturbance from the patient; (b) perturbations in the patient connection, such as leaks and partial occlusions; and (c) torque disturbances from the blower motor bearings and aerodynamic pressure load, among others. Similarly, patient-exhaled gas can flow through the blower to the ambient source can pre-load the blower pathway with gas enriched in oxygen. Subsequent rebreathing of the gas introduces additional oxygen over the desired set-point, further making mix control a challenging problem.

Further, ventilator controls often apply proportional-integral-derivative ("ND") compensators to stabilize and shape the transient response. Although variations in the patient pressure-flow dynamics can result in overshoot while using a PID compensator, the PID architecture itself can be the cause of overshoot since it applies either two real or a complex pair of zeros in the design which persist to influence the closed loop response.

Accordingly, there is a need in the art for non-invasive ventilator systems that more precisely control pressure and gas mixture in a stable manner while avoiding the many issues faced by current non-invasive ventilation designs.

SUMMARY OF THE INVENTION

The present disclosure is directed to inventive methods and systems for controlling pressure and gas mixture in a non-invasive ventilator system. Various embodiments and implementations herein are directed to a non-invasive ventilator system that controls blower pressure using a multi-level cascade feedback architecture. A complimentary filter is used for the feedback architecture, in which the filter blends machine and proximal pressure signals into a single signal for feedback. The non-invasive ventilation system also includes a mix controller that uses a mix estimator and separately determines the flow trajectory for the oxygen proportional valve flow servo to provide fast and accurate mix control that does not act as a disturbance to the blower pressure control system. The non-invasive ventilation system further includes a speed controller that utilizes a model-based motor speed observer to supplement tachometer speed readings at low speed.

Generally, in one aspect, a ventilator for controlling a pressure and gas mixture for an air flow is provided. The ventilator includes: (i) a gas source; (ii) a proportional valve configured to control a gas flow rate from the gas source; (iii) a mix controller in communication with the proportional valve and configured to monitor a flow of gas through the proportional valve, and further configured to control a percentage of oxygen in the air flow; (iv) a blower motor; and (v) a blower motor controller configured to control a speed of the blower motor using a blower speed feedback loop, a flow feedback loop, and a pressure feedback loop.

According to an embodiment, the mix controller and the blower controller are configured to cooperatively control the output flow.

According to an embodiment, the blower speed feedback loop is configured to linearize control of the speed of the blower motor and provide hard blower speed limitations without overshoot or windup.

According to an embodiment, the flow feedback loop is configured to minimize any disturbance of gas flow in the ventilator relative to target flow commanded by the pressure controller.

According to an embodiment, the pressure feedback loop is configured to track an applied pressure trajectory.

According to an embodiment, the ventilator further includes a pseudo-derivative compensator to eliminate compensator induced overshoot of the desired trajectory.

According to an embodiment, the pressure controller comprises a complimentary filter configured to blend a machine pressure signal and a proximal pressure signal into a single signal to the controller.

According to an embodiment, the ventilator further includes a speed controller configured to control the speed of the blower motor.

Generally, in one aspect, a ventilator is provided. The ventilator includes: (i) a blower motor controller configured to control the input current to the blower motor using a current feedback loop, a blower speed feedback loop, a flow feedback loop, and a pressure feedback loop, and further comprising a complimentary filter configured to blend a machine pressure signal and a proximal pressure signal into a single feedback signal for the pressure controller; (ii) a mix controller configured to monitor a flow of gas through a proportional valve, and gas derived from the blower and further configured to control a percentage of oxygen in the air flow to the patient; and (iii) a speed controller, the speed controller configured to control the speed of air flow.

Generally, in one aspect, a method for controlling the pressure and gas mixture for gas flow output, the method comprising the steps of: (i) providing a ventilator having a gas source, a proportional valve configured to control a gas flow rate from the gas source, a mix controller in communication with the proportional valve, a blower flow sensor, a blower motor, and a pressure controller, the pressure controller comprising a flow controller and a speed controller; (ii) activating the blower motor and opening the proportional valve to create flow and pressure in the ventilator; (iii) controlling, by the pressure controller, the speed of the blower motor using a blower speed feedback loop, flow feedback loop, and pressure feedback loop; (iv) monitoring, using the mix controller, a flow through the ventilator; and (v) adjusting, using the mix controller, the proportional valve flow to provide mix control.

According to an embodiment, the method further includes the step of adjusting, by the blower motor controller, the speed of the blower motor based on feedback of measured speed.

According to an embodiment, the method further includes the steps of: monitoring, using a speed controller, a speed of the blower; and adjusting, using the speed controller, the speed of the blower.

According to an embodiment, wherein the ventilator further comprises a complementary filter configured to blend a machine pressure signal and a proximal pressure signal into a single signal to the pressure controller.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

These and other aspects of the invention will be apparent from and elucidated with reference to the embodiment(s) described hereinafter.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION OF EMBODIMENTS

The present disclosure describes various embodiments of a ventilator system and method. More generally, Applicant has recognized and appreciated that it would be beneficial to provide a non-invasive ventilation system that accurately measures, adjusts, and controls pressure and gas mixture. For example, the non-invasive ventilation method and system utilizes multi-level cascade feedback control to control blower pressure. A complimentary filter is used for the feedback architecture, in which the filter blends machine and proximal pressure signals into a single signal for feedback. The system also includes a mix controller with a mix estimator, where the mix controller separately determines the flow trajectory for the oxygen proportional valve flow servo to provide fast and accurate mix control. The system also includes a speed controller that utilizes a model-based motor speed observer to supplement tachometer speed readings at low speed. The method and system result in more accurate control of both pressure and gas mixture in a non-invasive ventilator.

Although the methods and systems described below are applied to non-invasive ventilation, the methods and systems could similarly be utilized for any flow control system using proportional flow valves, especially where the throttling speed of the valve is significantly faster than the desired closed loop bandwidth of the flow controls.

Figure 1:
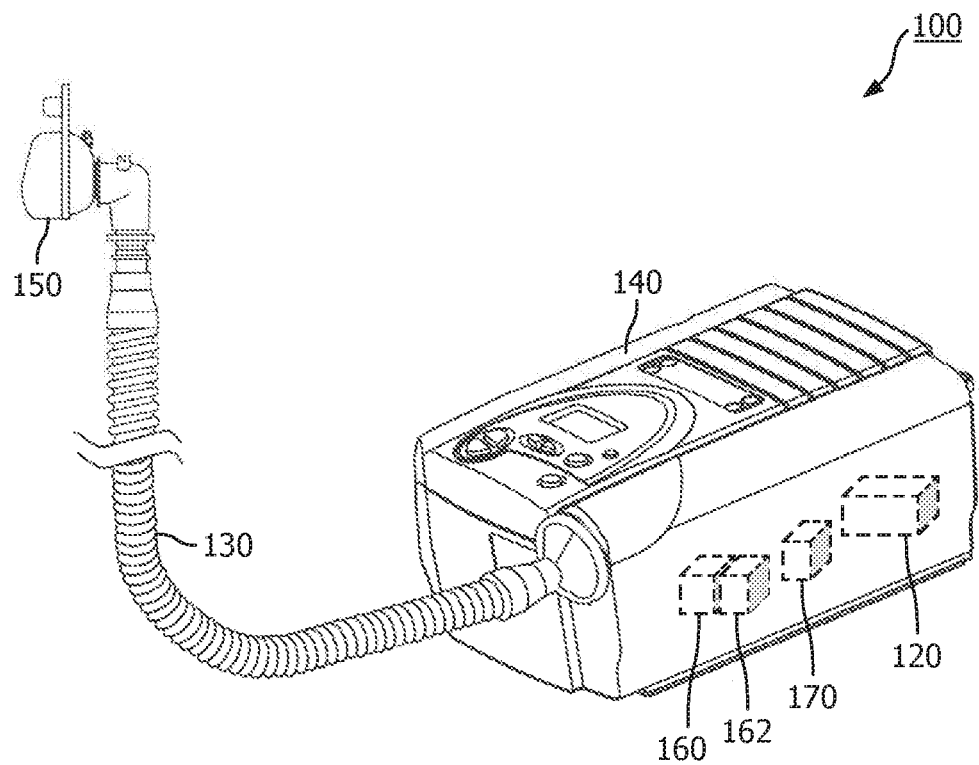
FIG. 1 is a schematic representation of a non-invasive ventilator system in accordance with an embodiment.

Referring to FIG. 1, in one embodiment, is a representation of an example non-invasive ventilation system 100. In this embodiment, the proportional valve introduces gas into the high pressure side, or outlet, of the blower, such that both the blower and proportional valve generate pressure. Also according to an embodiment, the system is a single limb ventilator such that there is a significant leak flow near the patient connection, and such that patient-exhaled gas has the potential to travel in a reverse direction through the blower during exhalation.

System 100 includes a gas source 220 (see FIG. 2) which can be any gas utilized for breathing, including but not limited to atmospheric air and oxygen, among others. The gas source is expelled from the ventilator with a predetermined pressure. The system also includes a controller 120, which is a conventional microprocessor, an application specific integrated circuit (ASIC), a system on chip (SOC), and/or a field-programmable gate arrays (FPGA), among other types of controllers. A controller may be implemented with or without employing a processor, and also may be implemented as a combination of dedicated hardware to perform some functions and a processor (e.g., one or more programmed microprocessors and associated circuitry) to perform other functions.

The controller 120 can be coupled with or otherwise in communication with any needed memory, power supply, I/O devices, control circuitry, and/or other devices necessary for operation of the system according to the embodiments described or otherwise envisioned herein. For example, in various implementations, a processor or controller may be associated with one or more storage media. In some implementations, the storage media may be encoded with one or more programs that, when executed on one or more processors and/or controllers, perform at least some of the functions discussed herein. Various storage media may be fixed within a processor or controller or may be transportable, such that the one or more programs stored thereon can be loaded into a processor or controller so as to implement various aspects of the present invention discussed herein. The terms "program" or "computer program" are used herein in a generic sense to refer to any type of computer code (e.g., software or microcode) that can be employed to program one or more processors or controllers.

According to an embodiment, the system includes a tube or tubing 130 that delivers gas from the remote ventilator component 140 to the user interface 150. User interface 150 can be, for example, a face mask that covers all or a portion of the user's mouth and/or nose. There may be masks of many different sizes to accommodate patients or individuals of different sizes, and/or the mask may be adjustable. As another alternative, user interface 150 may fit within or on, or otherwise interact with, a tracheostomy tube. Accordingly, the user interface 150 may be a variety of sizes to accommodate tracheostomies of different shapes and sizes. The user interface is configured to fit with at least a portion of the patient's airway.

System 100 also includes a blower 160 with a motor, which together with a proportional valve system 200 (shown in FIG. 2) generates flow and pressure for the system. The blower motor is controlled by blower motor controller 162, which can control, for example, the speed of the motor. According to an embodiment, the blower motor is a component of the blower, which can include an impeller, housing, and motor. The flow and pressure of the system is determined in part by the speed of the blower motor, which in turn is controlled by the blower motor controller 162. The blower motor controller 162 can be the same controller as controller 120, or can be a separate controller preferably in communication with controller 120. The controller can be any processor, and can be coupled with or otherwise in communication with any needed memory, power supply, I/O devices, control circuitry, and/or other devices necessary for operation of the system according to the embodiments described or otherwise envisioned herein.

Figure 2:
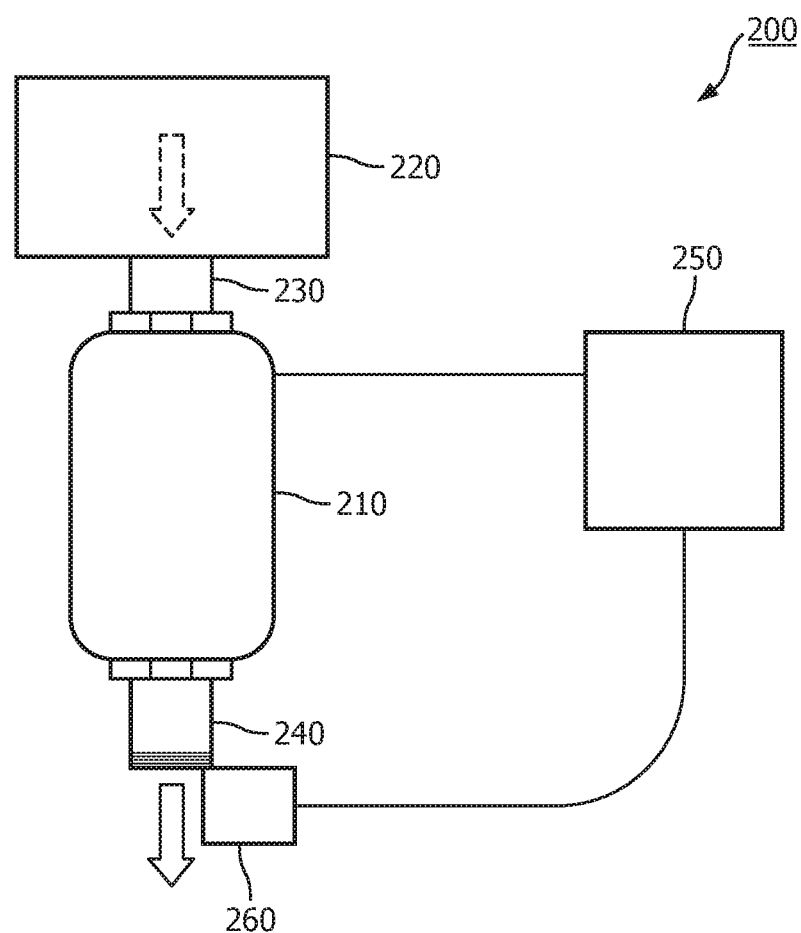
FIG. 2 is a schematic representation of a proportional flow valve system in accordance with an embodiment.

According to an embodiment, system 100 uses both ambient air and high-pressure oxygen. The ambient air enters through an inlet filter, and the oxygen enters through a high-pressure inlet which is controlled by a proportional valve system 200. Accordingly, in order to control the flow and pressure of gas in the ventilator, system 100 must precisely control both the speed of the blower motor and the operation of the proportional valve system. Referring to FIG. 2, in one embodiment, is the proportional valve system 200. The proportional valve system includes a proportional valve 210, which may be any proportional valve known in the art. Many different types of proportional valves exist, including screw-type proportional valves, electromagnetic proportional valves, and many other types of proportional valves. Any of these valves may be utilized in the system 200. The proportional valve system also includes a high-pressure gas source 220. The gas source can be any gas source that might be utilized, such as surrounding environmental air, an oxygen tank, a nitrogen tank, mixtures thereof, as well as a very wide variety of other gas sources. There is no requirement that the gas be breathable by humans, and thus the gas source could be toxic or other gases. Gas from gas source 220 exits the gas source via 230, and exits through outlet 240, if proportional valve 210 is at least partially open. Proportional valve 210 controls the amount of gas that exits the gas source, as well as the rate at which the amount of gas exits the gas source.

The proportional valve system includes a controller 250, which can be the same controller as controller 120, or can be a separate controller preferably in communication with controller 120. The controller can be any processor, and can be coupled with or otherwise in communication with any needed memory, power supply, I/O devices, control circuitry, and/or other devices necessary for operation of the system according to the embodiments described or otherwise envisioned herein. Although controller 250 is shown as being separate from proportional valve 210 in FIG. 2, according to other embodiments the controller can be attached to the exterior of the valve, can be an integral component of the valve, completely remote from the valve, or in some other physical relationship with the valve. In the case where the controller is remote from the valve, communication can be transmitted wirelessly between the controller and the valve.

Controller 250 controls proportional valve 210, and thus controls the amount of gas that exits the gas source, as well as the rate at which the amount of gas exits the gas source. The controller can be directed by an external source such as a user, and/or can be directed by programming. For example, a user can push a button or provide some other input indicating that the flow should increase, and the controller receives that signal and provides a signal to the proportional valve to increase the flow. Alternatively, the controller or an associated processor is programmed or configured to reduce or increase flow according to a specific time, response, or other input. System 200 also includes a flow sensor 260. The flow sensor detects the flow of gas after it exits the proportional valve 210. According to an embodiment, the proportional valve system 200 is a component of ventilator 100, as shown in FIG. 2. Accordingly, the output 240 can be or connect to tubing 130 that leads to the patient.

Figure 3:
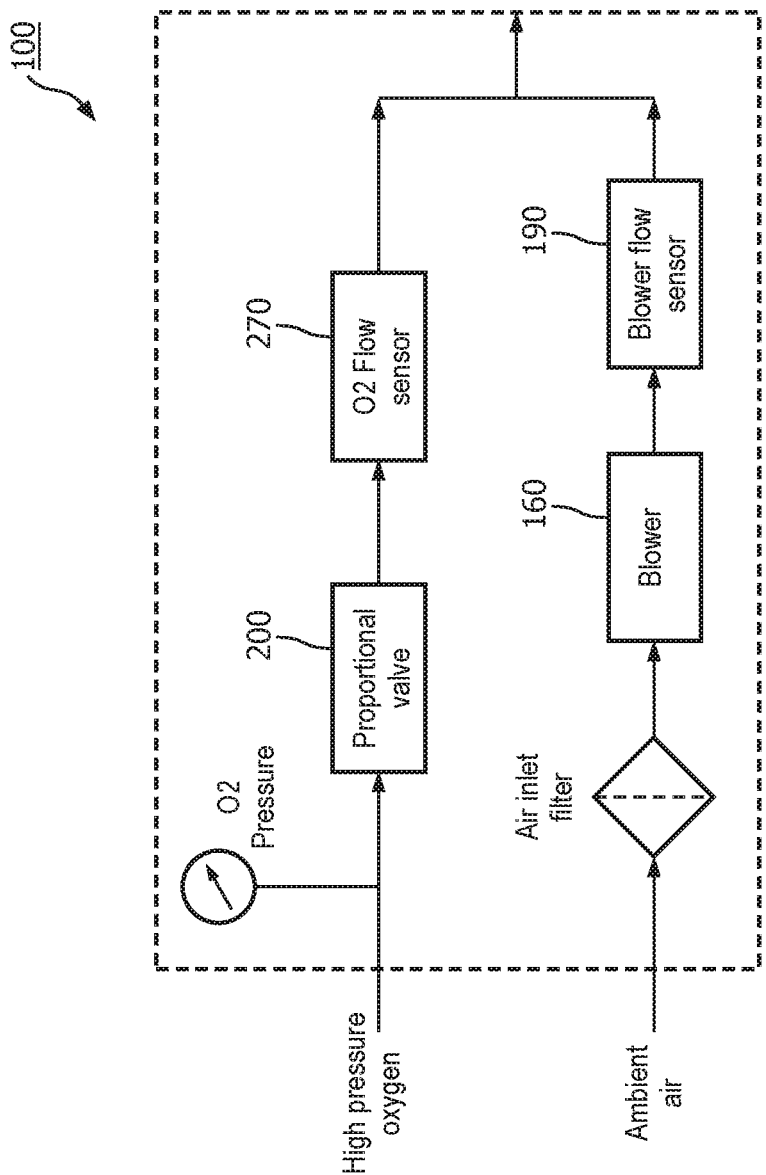
FIG. 3 is a schematic representation of a non-invasive ventilator system in accordance with an embodiment.

Referring to FIG. 3, in one embodiment, is a representation of an example non-invasive ventilation system 100 with a blower 160 and a proportional valve system 200, which includes a proportional valve controlled to set and adjust the flow of high-pressure gas into the system. In this embodiment, the proportional valve introduces high-pressure gas, such as oxygen, into the system. The action of blower 160 pulls ambient air into the system where it is pressurized in the blower, mixed with oxygen from the proportional valve system, and then delivered to the patient. The ventilator system may also include a gas flow sensor 270 to detect the flow of high-pressure gas. The information from gas flow sensor 270 can be used, for example, to analyze and/or adjust the proportional valve 210 in order to deliver the correct flow of gas. The ventilator system 100 can also include, for example, an air flow sensor 190 that detects the flow of ambient air into the blower 160. The information from air flow sensor 190 can be used to analyze and/or adjust the blower 160 to ensure that the correct air flow is delivered. Alternatively, either of gas flow sensor 270 and air flow sensor 190 can be used to detect an error in the supply of the gas or air, respectively. Ambient air and high-pressure gas arrive in a manifold where the two gases are mixed. The mixed gas then goes to the patient. The mixed gas is pressurized by both the blower 160 and the proportional valve 210 before being delivered to the patient 100. Although the system is depicted in FIG. 3 with a specific configuration, many variations to this configuration are possible.

Figure 4:
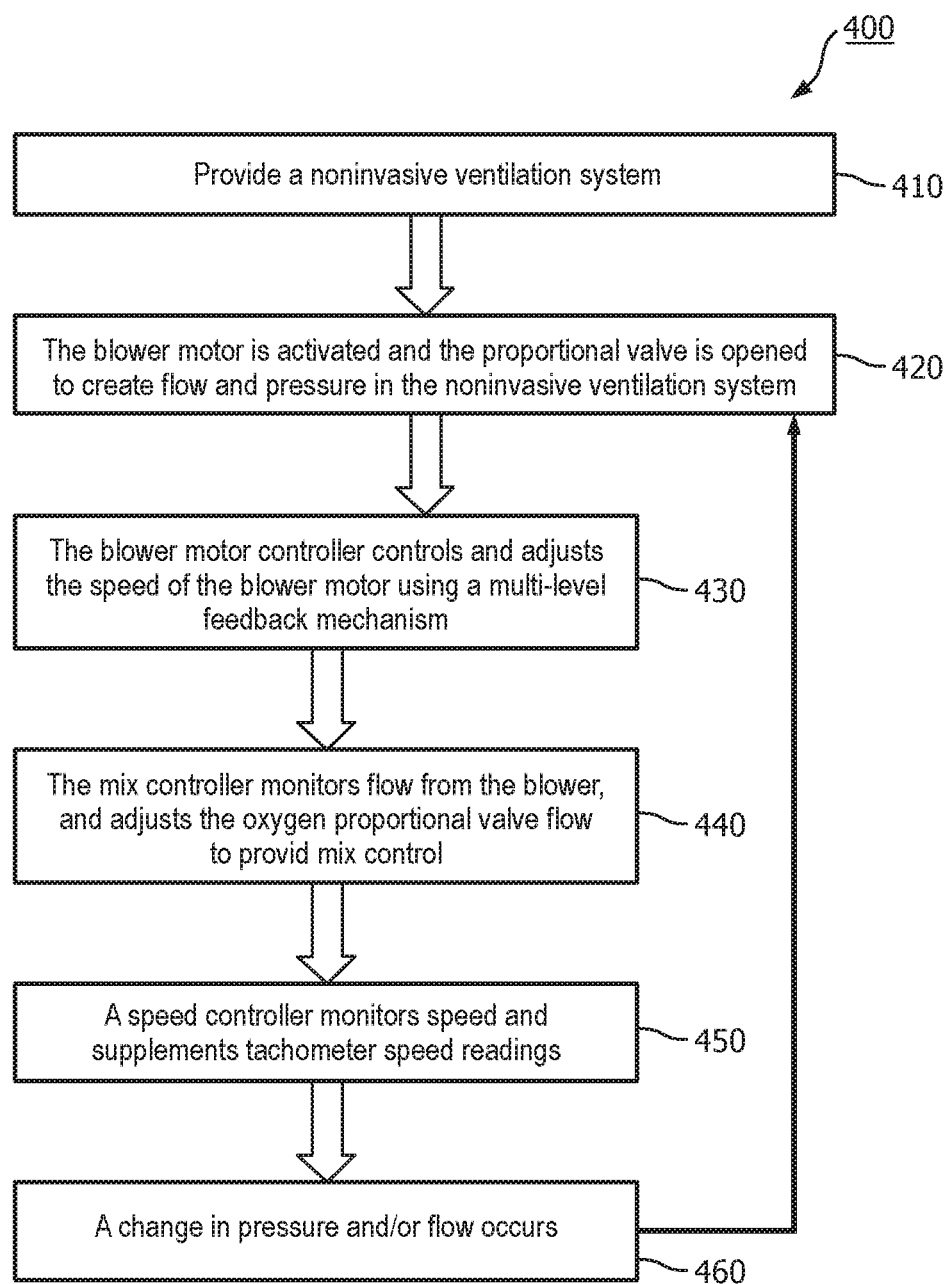
FIG. 4 is a flowchart of a method for controlling pressure and gas mixture in a non-invasive ventilator system, in accordance with an embodiment.

Referring to FIG. 4, in one embodiment, is a flowchart of a method 400 for controlling pressure and gas mixture in a non-invasive ventilator system. At step 410, a noninvasive ventilation system 100 is provided. The system is any of the noninvasive ventilation systems described or otherwise envisioned herein, and can include, for example, a controller 120, a blower 160, a blower motor controller 162, a proportional valve 210, a proportional valve controller 250, a gas source 220, and a flow sensor 260, among other components. Other embodiments are also possible.

At step 420 of the method, the ventilation system 100 is activated and the controller 120 directs blower motor controller 162, which can be the same controller, to activate the blower motor to blow ambient air into the system. The controller 120 also directs proportional valve controller 250, which can be the same controller, to open the proportional valve 210 to allow the high-pressure gas to enter the system. Together, the activated blower 160 and the opened proportional valve 210 create flow and pressure, and by their flow ratio, a particular gas mixture within the system.

Figure 5:
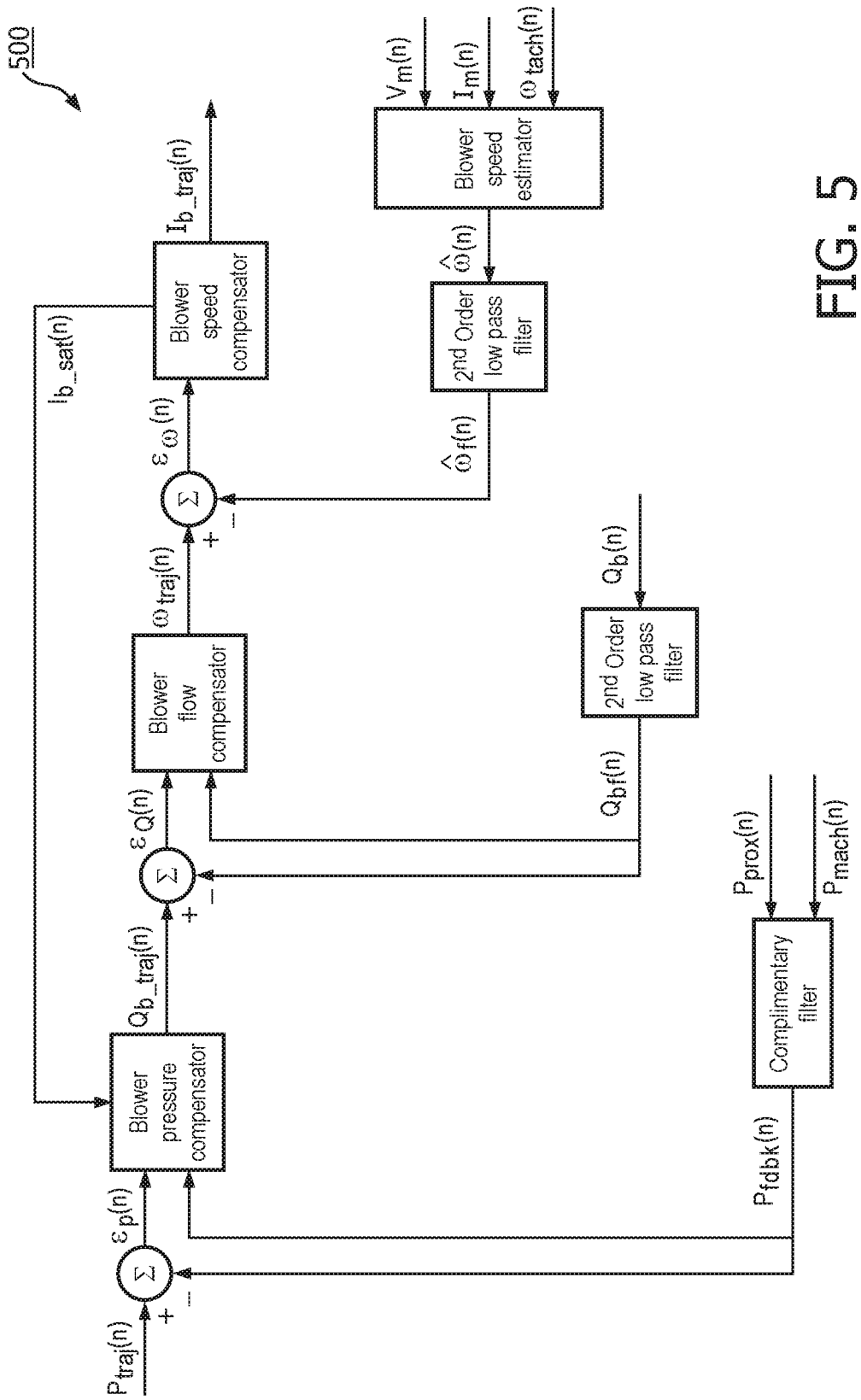
FIG. 5 is a schematic representation of a blower pressure control system for a non-invasive ventilator system, in accordance with an embodiment.

At step 430 of the method, blower motor controller 162 controls and adjusts the speed of the blower motor using a multi-level feedback mechanism 500. Referring to FIG. 5, in one embodiment, is a schematic representation of the multi-level feedback mechanism. According to an embodiment, the system 100 must accommodate a wide range of speeds and load dynamics for accurate pressure tracking and maintenance. The system may also need to tolerate flow disturbance while regulating the pressure trajectory, among other control requirements. In order to meet these requirements, the system 100 utilizes a cascade control architecture with four nested feedback control loops: (1) a current feedback loop; (2) a blower speed feedback loop; (3) a flow feedback loop; and (4) a pressure feedback loop. This architecture maximizes inner-loop stiffness and manages disturbance rejection at each sub-level such that the pressure controls at the top most level are able to achieve high performance. According to an embodiment, the current feedback loop minimizes the influence of back electromotive force ("back-emf") and overcomes the intrinsic electrical time constant of the motor. The blower speed feedback loop can linearize speed controls, reject motor load disturbances, and hard-limit to maximum speed constraints with high precision. The flow feedback loop helps reject pressure disturbing influences caused by patient flow demand, cough, and partial circuit occlusions. And at the top level, the pressure feedback loop accurately tracks the applied pressure trajectories. The system can also include a pseudo-derivative ("PDF") compensator for pressure control that eliminates overshoot caused by PID zeros, but retains the characteristic stability traits of the PID. The flow loop compensator is also PDF, the speed loop is PID.

According to an embodiment, a complimentary filter is provided for the blower motor controller 162 and is used for feedback. The filter blends the machine and proximal pressure signals into a single signal for feedback. According to an embodiment, blending is done across complimentary frequency bands: the proximal sensor at low frequency and the machine sensor at higher frequencies. The machine signal, with less delay provides a stable, but faster blower response, and the prox signal (which is the pressure measurement at the proximal patient connection), accurate proximal pressure at steady state.

At step 440 of the method, a mix controller 170 monitors the size and direction of flows through the circuit and blower, and adjusts the oxygen proportional valve flow to provide mix control. According to an embodiment, the mix controller separately determines the flow trajectory for the oxygen proportional valve flow servo providing fast and accurate mix control. For example, the mix controller can correct mix if it detects an error in the current mix. According to an embodiment, the mix correction consists of a feedback controller with a PI compensator that works together with the feedforward part of the controller. According to an embodiment, the mix controller also compensates for the rebreathing issue by closely keeping track of the size and direction of flow sources through the internal manifolds. It determines how much the gas in the blower pathway is enriched by the rebreathing, and the mix controller reduces the oxygen flow to compensate. A feed-forward path is used for fast response to the set mix, and slower feedback for high accuracy in the steady state.

Figure 10:
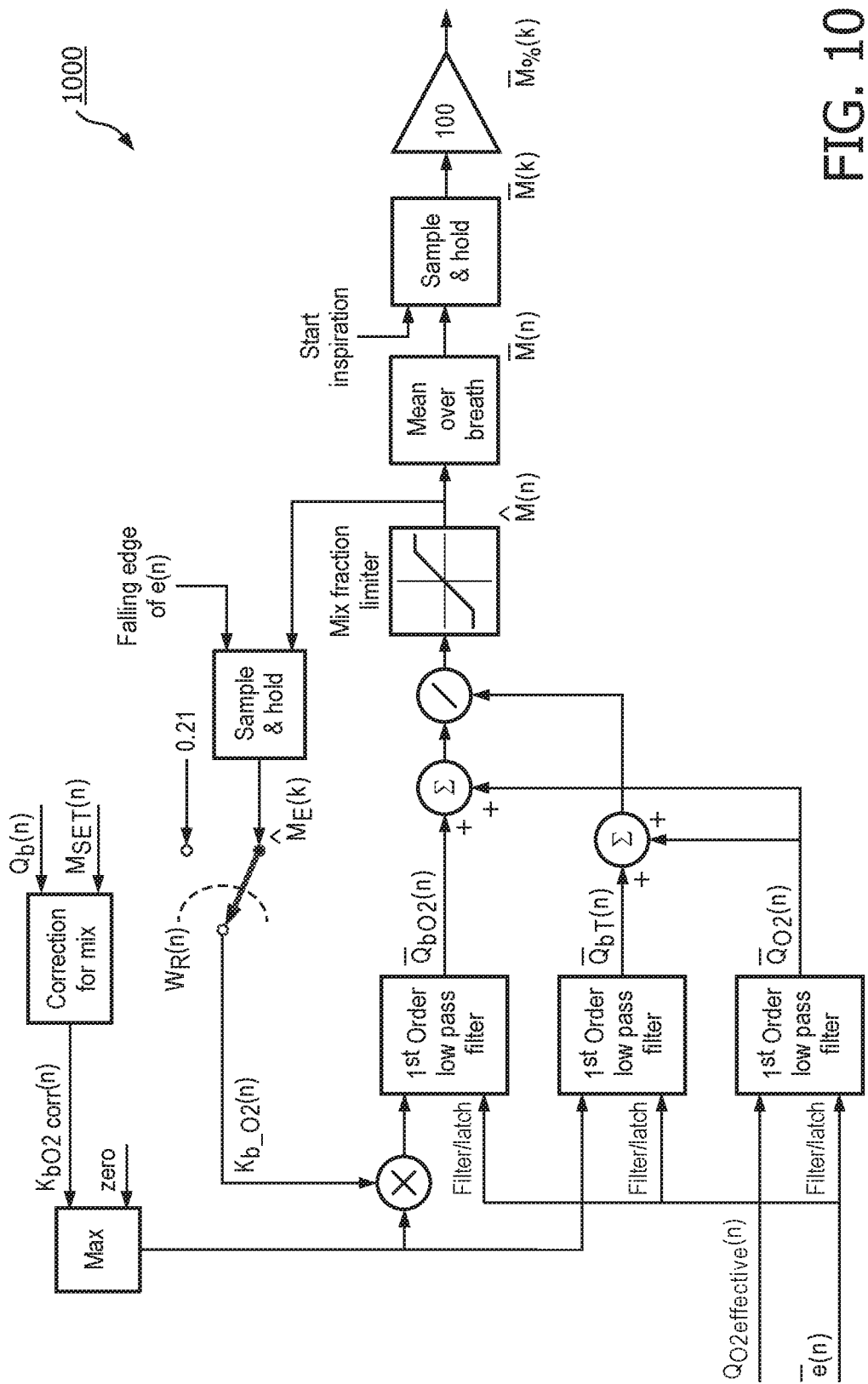
FIG. 10 is a schematic representation of a non-invasive ventilator mix controller mix estimator, in accordance with an embodiment.

According to an embodiment, the mix controller utilizes a mix estimator that provides a feedback estimate for $O_2$ correction by the mix controller, and that closely monitors the size and direction of flows through the circuit and blower. Referring to FIG. 10, in one embodiment, is a schematic representation of a mix estimator 1000.

At step 450, a speed controller monitors speed and supplements tachometer speed readings at low speed, providing the ability to control blower speed at very low rates. According to an embodiment, the speed controller bridges flow and current controllers and rejects viscous frictional and torque related disturbances. The speed controller relies on a model based motor speed observer to supplement the tachometer speed readings at low speed. This can greatly improves the ability to control pressure transients during exhalation with the blower.

At step 460, a change in pressure and/or flow occurs and the system adapts by, for example, increasing or decreasing mix, increasing or decreasing pressure by the proportional valve system, and/or by increasing or decreasing the speed of the blower motor. The change in pressure and/or flow can be a request for a change, such as a change in the setting of the ventilator. The change can be the result of a leak in the system, or a change in the ventilator user's condition, position, or other change. The system 100 detects the change and determines, using the controller or controllers and the methods described herein, to adjust the system and return the pressure and/or flow to the proper setting.

Non-Invasive Ventilation Pressure Control

Referring to FIG. 5, in one embodiment, is a schematic representation of a cascade pressure controller 500, with a speed loop, flow loop, and pressure loop. Non-invasive ventilation pressure controls utilize gas sources from the blower and oxygen valve providing mixed gas support to the patient through a single limb circuit with expected leaks. To overcome limiting dynamic differences in the system, an alternate approach to mixing is used called "slaving." In slaving the oxygen flow servo loop is made to follow a flow trajectory that is determined by a fraction of the measured total flow. Details of the slaving algorithm are provided below, but first it is important to also consider an issue that affects the non-invasive ventilation pressure control mix, namely rebreathing of patient exhaled gas within the blower pathway. For the single limb circuit system, and certain settings and patient loading, gas during exhalation can reverse direction through the blower pathway, enriching that pathway with oxygen for the subsequent breath. It is essential that mix controls take rebreathing into account to meet mix accuracy.

According to an embodiment, the system also needs to accommodate a wide range of load dynamics for accurate pressure tracking. The system may also need to tolerate flow disturbance while regulating the pressure trajectory. To meet such capabilities, and to provide strict speed limiting ability, a cascade control architecture can be utilized. According to an embodiment, the cascade architecture comprises three nested feedback control loops: (i) a speed loop; (ii) a flow loop; and (iii) a pressure loop.

According to an embodiment, the most inner loop provides as its output the blower current command and receives as its input a speed trajectory from the flow loop at the next upper level, and blower speed, current and voltage measurements to estimate blower speed for feedback. The speed loop maintains internal anti-windup control, but also provides an output signal that feeds back to the pressure controller to 'wind-down the pressure controller integrator in the event the speed loop reaches saturation limits. The flow loop receives as its input a flow trajectory from the pressure loop, the outermost loop in the cascade and a measurement of the blower flow as feedback. The pressure loop receives as its inputs a pressure trajectory from any particular ventilation mode (PC, PPV, etc.), proximal and machine pressure measurements that are blended by the complimentary filter for feedback, and the saturated speed signal from the speed loop. The cascade approach to control can be leveraged where a process is able to provide more than one relevant measurement in meeting a primary control goal. By considering intermediate feedback signals, the process can be engineered for improved tracking and disturbance rejection. For pressure controls the pressure, flow, and speed measurements are considered for cascade control.

According to an embodiment, the inner speed loop has an anti-windup feature that communicates locally and back to the outer pressure loop, providing immediate recovery from saturation at maximum or minimum speed. This nonlinear control provision allows the blower to accelerate as quickly as the current limitations will allow without overshoot or loss of control. According to an embodiment, the speed loop feedback signal can be provided by a combined X6 Hall tachometer signal for high speed and a model based estimator for low speed and all the way to zero offering 1 kHz sample rate, free from aliased phase ripple. The middle loop flow feedback controller helps to reject flow disturbances in the pressure control loop and helps provide additional damping action for the pressure loop control.

Figure 6:
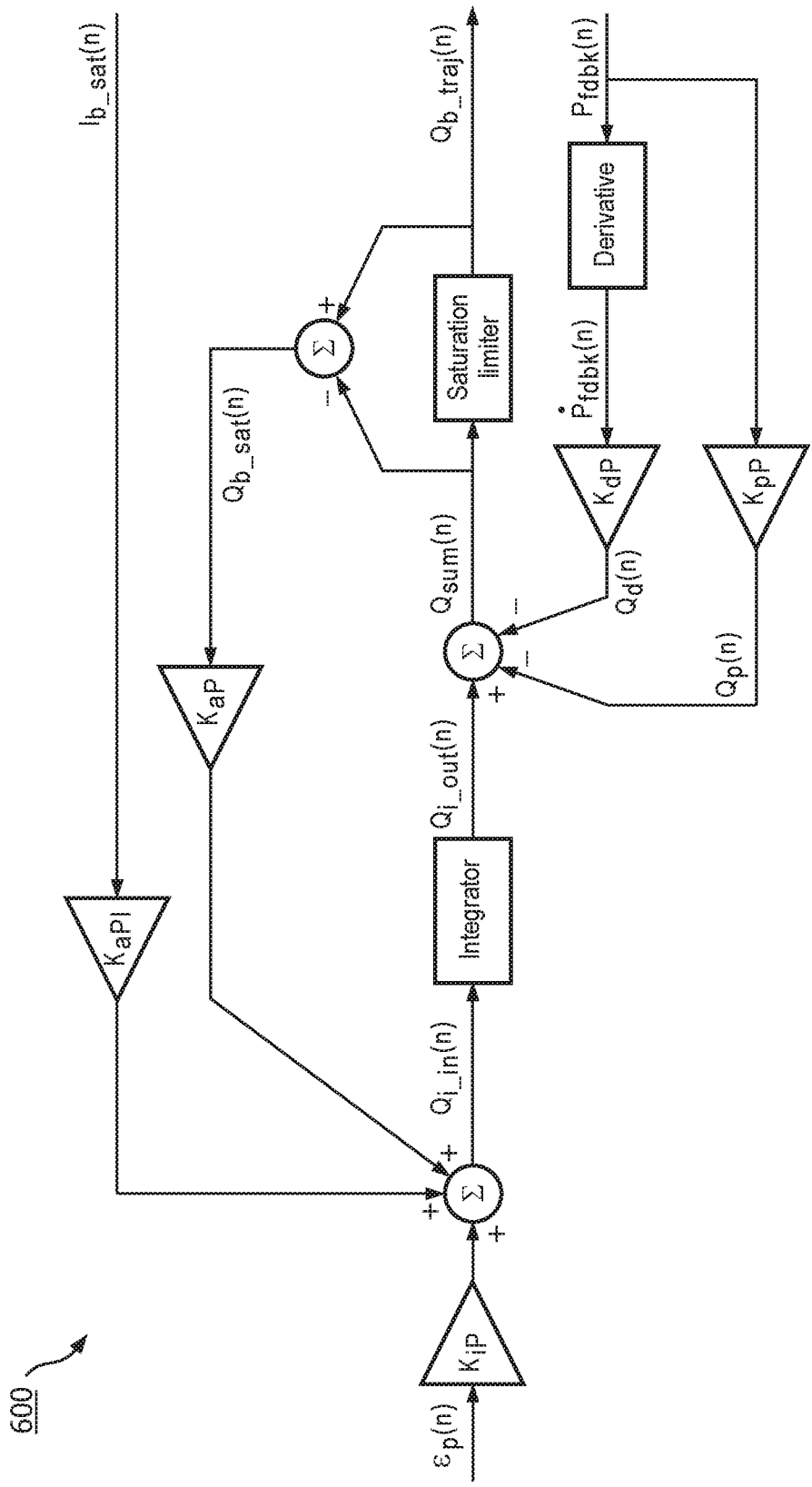
FIG. 6 is a schematic representation of a model for a non-invasive ventilator blower pressure control loop compensator, in accordance with an embodiment.

According to an embodiment, the dynamics of the pressure and slave mix control are tightly intertwined in terms of the load they manage and must be considered together functionally in achieving required stability and performance, but the two controllers are topologically separate from one another and so can be described separately. Note that FIGS. 5 and 6 illustrate the general structure of the controller components, and the connections between them. However, each component of the cascade control, the pressure, flow, and speed compensators are discussed in further detail below.

Non-Invasive Ventilation Pressure Compensator

Referring to FIG. 6, in one embodiment, is a schematic representation of the blower pressure control loop compensator 600. While machine pressure affords the best measure of pressure with respect to stability in the control, the intended reference frame for control is the more remote proximal patient connection. But the greater separation in distance between flow actuation and pressure measurement at the proximal patient connection ("prox" or "$P_{prox}$") causes significant transport delay in the feedback loop. This delay typically requires lower loop gain to achieve stable operation, and thus a reduction in performance (rise time, overshoot, etc.) is expected. Operating in the prox pressure frame of reference can be a requirement and so to recover both stability and performance, a complimentary filter can be used that blends the two pressures together as a single pressure measurement. Tracking error between pressure trajectory and proximal pressure is most important at steady state (and to some degree lower frequencies), and the crossover frequencies for stability margins typically occur at the higher range of frequencies. Therefore the proximal and machine pressures can each be processed by filters that isolate information over separate frequency bands, however combined to provide the full band more effective for feedback control than if either were taken independently.

According to an embodiment, the complimentary filter is realized using a construct of the generalized filter to serve as a low pass filter for the $P_{prox}$ component of feedback pressure, $P_{fdbk}$, and a band pass filter for the $P_{mach}$ component. Specification of the complimentary filter requires definition of a cross frequency, $\omega_x$, where the magnitude frequency responses of the low pass and band pass filters intersect:

$$P_{fdbk}(n) = \begin{cases} F_{BP}(n) + F_{LP}(n) & \text{for normal operation} \\ P_{mach}(n) & \text{for } prox \text{ line disconnect or occlusion} \end{cases} \quad \text{(Eq. 1)}$$

Prox line disconnect or occlusion can be determined by the disconnect and occlusion algorithm (not described in this disclosure). For $F_{LP}(n)$, a generalized filter may be used with the following settings: a=0; b=$\omega_x$=6.28 rad/sec (1 Hz); c=1; d=$\omega_x$; $\Delta T$=0.001 sec; the generalized filter input at x(n)= $P_{prox}(n)$; and the generalized filter output at y(n)=$F_{LP}(n)$. For $F_{BP}(n)$, a band pass filter may be used with the following settings: $\omega_{low}$=$\omega_x$; $\omega_{high}$=2513.3 rad/sec (400 Hz); $\Delta T$=0.001 sec; and set the band pass filter input, u(n)=$P_{mach}(n)$; and set the band pass filter output, v(n)=$F_{BP}(n)$. According to an embodiment, the pressure controller servo error, $\varepsilon_p(n)$ is the difference of the pressure trajectory, $P_{traj}(n)$ and the measured (raw) pressure, $P_{fdbk}(n)$:

$$\varepsilon_p(n)=P_{traj}(n)-P_{fdbk}(n) \qquad \text{(Eq. 2)}$$

Pressure Loop PDF Compensator

According to an embodiment, the basic structure of the pressure loop compensator uses the pseudo-derivative feedback structure. This structure accomplishes the same closed loop dynamics as if a PID compensator were used however the PDF structure eliminates the zeroes introduced in the PID, and consequently any overshoot introduced by the controller itself. FIG. 6 illustrates that the input to the integrator, $Q_{i\_in}(n)$, is calculated by summing the anti-windup feedback components from the speed and pressure controller and the product of integral gain, $K_{iP}$, and the pressure servo error, $\varepsilon_p(k)$:

$$Q_{i\_in}(n)=K_{aPI}I_{b\_sat}(n)+K_{aP}Q_{b\_sat}(n)+K_{iP}\varepsilon_p(n) \qquad \text{(Eq. 3)}$$

According to an embodiment the following gains can be used: $K_{iP}$=300 lpm/cm $H_2O$; $K_{aP}$=10 sec$^{-1}$; and $K_{aPI}$=10 sec$^{-1}$. The integration is approximated in discrete time by a forward difference. The integrator output, $Q_{i\_out}(n)$ is calculated as:

$$Q_{i_{out}}(n)=\Delta T Q_{i\_in}(n-1)+Q_{i\_out}(n-1) \qquad \text{(Eq. 4)}$$

and the initial condition $Q_{i\_in}(0)$=0. The integrator is never reset after start-up.

The feedback components of pressure include scaled values of the filtered machine pressure, $Q_p(n)$ and the time rate of change of pressure, $Q_d(n)$, with the latter being estimated by a filtered derivative of the machine pressure. According to an embodiment, the methods described herein may be utilized to calculate these components, by substituting the following assigned variables and parameters. For the derivative of the feedback pressure, $\dot{P}_{fdbk\_f}(n)$, the following derivative is utilized.

$$\dot{P}_{fdbk}(n) = \frac{(p_{fdbk}(n) - P_{fdbk}(n-1))}{\Delta T} \qquad \text{(Eq. 5)}$$

The raw flow control command, $Q_{sum}(n)$, is then calculated as the sum and difference of the integrator output and feedback components:

$$Q_{sum}(n)=Q_{i\_out}(n)-K_{dP}\dot{P}_{fdbk}(n)-K_{pP}P_{fdbk}(n) \qquad \text{(Eq. 6)}$$

where $K_{dP}$=0.15 lpm-sec/cm $H_2O$; and $K_pp$=12 lpm/cm $H_2O$. The output of the pressure compensator, the blower flow trajectory, $Q_{b\_traj}(n)$ is constrained by flow limits:

$$Q_{b\_traj}(n) = \min\{Q_{b\_trajMax}, \max\{Q_{b\_trajMin}, Q_{sum}(n)\}\} \qquad \text{(Eq. 7)}$$

where: $Q_{b\_trajMax} = 250 \ lpm$ and $$Q_{b\_trajMin} = \begin{cases} 0 \ lpm & \text{for inhalation phase} \\ -250 \ lpm & \text{for exhalation phase} \end{cases}.$$

Lastly, the saturation difference is calculated to complete the loop for pressure anti-windup due to flow limits:

$$Q_{b\_sat}(n)=Q_{b\_traj}(n)-Q_{sum}(n) \qquad \text{(Eq. 8)}$$

Non-Invasive Ventilation Blower Flow Compensator

Figure 7:
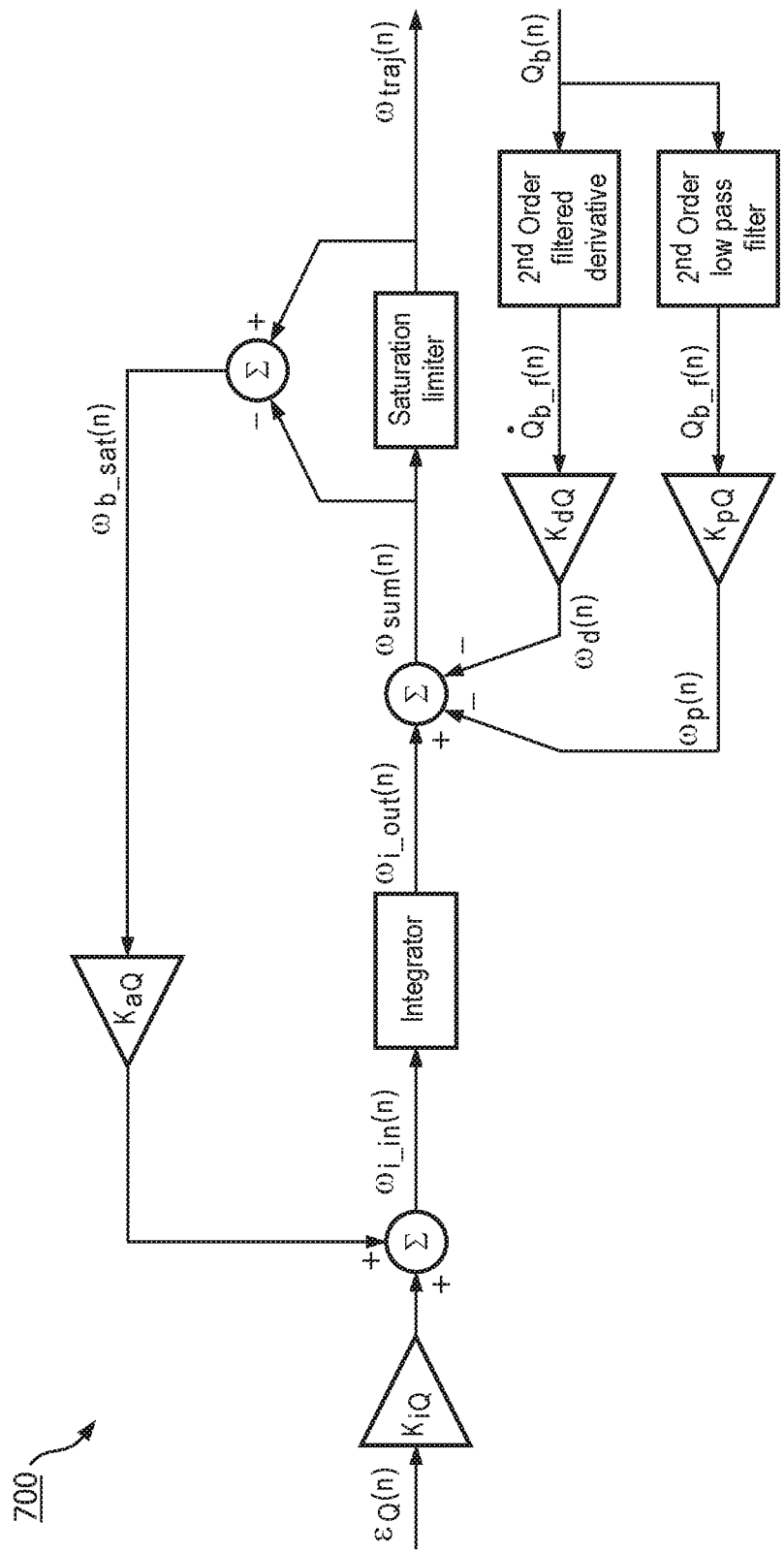
FIG. 7 is a schematic representation of a model for a non-invasive ventilator flow loop compensator, in accordance with an embodiment.

According to an embodiment, the flow controller is designed to couple the pressure and blower speed control loops and provide some conditioning to the pressure control based on the way flow is responding. This conditioning provides damping of the pressure controls, and also provides greater insulation of pressure controls from flow disturbances. Referring to FIG. 7, in one embodiment, is a schematic representation of a flow loop compensator 700 which is based on the PDF structure.

Before feedback is used to calculate the flow servo error, the raw blower flow measurement, $Q_b(n)$, can first be filtered to reduce high frequency noise using a $2^{nd}$ order low pass filter. To obtain the filtered blower flow measurement, $Q_{bf}(n)$, the following signal substitutions and parameter settings can be utilized: x(n)=$Q_b(n)$; y(n)=$Q_{bf}(n)$; $\omega_o$=3000 rad/sec; $\zeta$=0.707; and $\Delta T$=0.001 sec. As illustrated in FIG. 7, the flow controller servo error, $\varepsilon_Q(k)$, can be calculated as the difference between the blower flow trajectory, $Q_{b\_traj}(n)$, and the scaled, filtered blower flow measurement, $Q_{bf}(n)$:

$$\varepsilon_Q(n)=Q_{b\_traj}(n)-Q_{bf}(n) \qquad \text{(Eq. 9)}$$

FIG. 7 shows that the input to the integrator, $\omega_{i\_in}(n)$ is calculated by summing the anti-windup feedback and the product of integral gain, $K_{iQ}$ and the flow servo error, $\varepsilon_Q(n)$:

$$\omega_{i\_in}(n)=K_{aQ}\omega_{b\_sat}(n)+K_{iQ}\varepsilon_Q(n) \qquad \text{(Eq. 10)}$$

where the following gains are used: $K_{aQ}$=10 sec-1; and $K_{iQ}$=2000 rpm/lpm-sec. The integration is approximated in discrete time by a forward difference. The integrator output, $\omega_{i\_out}(n)$ is calculated as:

$$\omega_{i_{out}}(n)=\Delta T^*\omega_{i\_in}(n-1)+\omega_{i\_out}(n-1) \qquad \text{(Eq. 11)}$$

and the initial conditions $\omega_{i\_in}(0)$=0 and $\omega_{i\_out}(0)$=2000. According to an embodiment, the integrator is not reset after start-up.

The feedback components of flow include scaled values of the filtered blower flow, $Q_{b\_f}(n)$, and the filtered derivative of flow, $\dot{Q}_{b_f}(n)$, as shown in FIG. 7. The following assigned variables and parameters can be used. For filtered blower flow, $Q_{b\_f}(n)$; x(n)=$Q_b(n)$; y(n)=$Q_{b\_f}(n)$; $\omega_o$=1500 rad/sec; $\zeta$=0.707; $\Delta T$=0.001 sec. For the filtered derivative of blower flow, $\dot{Q}_{b\_f}(n)$; x(n)=$Q_b(n)$; y(n)=$\dot{Q}_{b\_f}(n)$; $\omega_o$=1500 rad/sec; $\zeta$=0.707; $\Delta T$=0.001 sec. The raw speed control command, $\omega_{sum}(n)$ can then be calculated as the sum and difference of the integrator output and feedback components and the sum of the pressure error feedforward:

$$\omega_{sum}(n)=\omega_{i\_out}(n)-K_{dQ}\dot{Q}_{bf}(n)-K_{pQ}Q_{bf}(n) \qquad \text{(Eq. 12)}$$

where $K_{dQ}$=0.15 rpm-sec/lpm; and $K_{pQ}$=0.0 rpm/lpm. The output of the blower flow compensator, the blower speed trajectory, $\omega_{traj}(n)$ is constrained by speed limits:

$$\omega_{traj}(n)=\min\{\omega_{trajMax},\max\{\omega_{trajMin},\omega_{sum}(n)\}\} \qquad \text{(Eq. 13)}$$

where to $\omega_{trajMax}$=50,000 rpm; and $\omega_{trajMin}$=2000 rpm. Note that the speed controller is capable of controlling below 2000 rpm, but according to an embodiment this lower limit was chosen to provide the best response on recovery after saturation. Lastly, the saturation difference is calculated to complete the loop for flow anti-windup due to the speed limits:

$$\omega_{b\_sat}(n)=\omega_{traj}(n)-\omega_{sum}(n) \qquad \text{(Eq. 14)}$$

Blower Speed Controller

According to an embodiment, the blower speed control provides control of blower speed for stiff flow throttling but also helps reduce the chance of motor current amplifier shutdown due to over-speed conditions. This can be accomplished, for example, by tightly following the speed trajectory, providing zero overshoot, and rapid saturation recovery. The speed controller can use, for example, a hybrid method of blower speed measurement where an improved X6 tachometer reading is used at high speed and a model based estimator at lower speed. The hybrid approach provides a low noise speed signal that responds over the full range with a 1 kHz update including accurate speed estimation that operates down to near zero speed. If the tachometer were used by itself, the sample rate on 6 Hall transitions works out to be only about 200 Hz. By utilizing the estimated speed from current and voltage, the 1 kHz sampling of motor speed is maintained all the way to near zero speed. By not using the speed estimated by current and voltage above 10000 rpm, and rather only the tachometer signal, the feedback signal is protected from seeing aliased motor harmonics specifically motor cogging also known as torque pulsations. The lower range of speed control provides improved control of the pressure transient into expiratory positive airway pressure ("EPAP").

According to an embodiment, the controller can include an integrator as part of the compensator for speed trajectory tracking accuracy, as well as aggressive anti-windup control that communicates to both the local integrator in the speed control and the integrator in the pressure controller. The anti-windup design allows the controller to operate in saturation during blower acceleration to minimize rise time and to provide immediate recovery under linear control to accurately track the speed trajectory. According to an embodiment, the only time the controller cannot track the trajectory is during rapid deceleration. For rapid deceleration, the motor two-quadrant current controller brakes or otherwise slows the motor speed by using a limited source of electrical power stored in capacitors. But once the current controller recovers from braking, the speed controller and its stiff anti-windup mechanism provide the best chance of locking locks onto the speed trajectory.

Blower Speed Compensator

Figure 8:
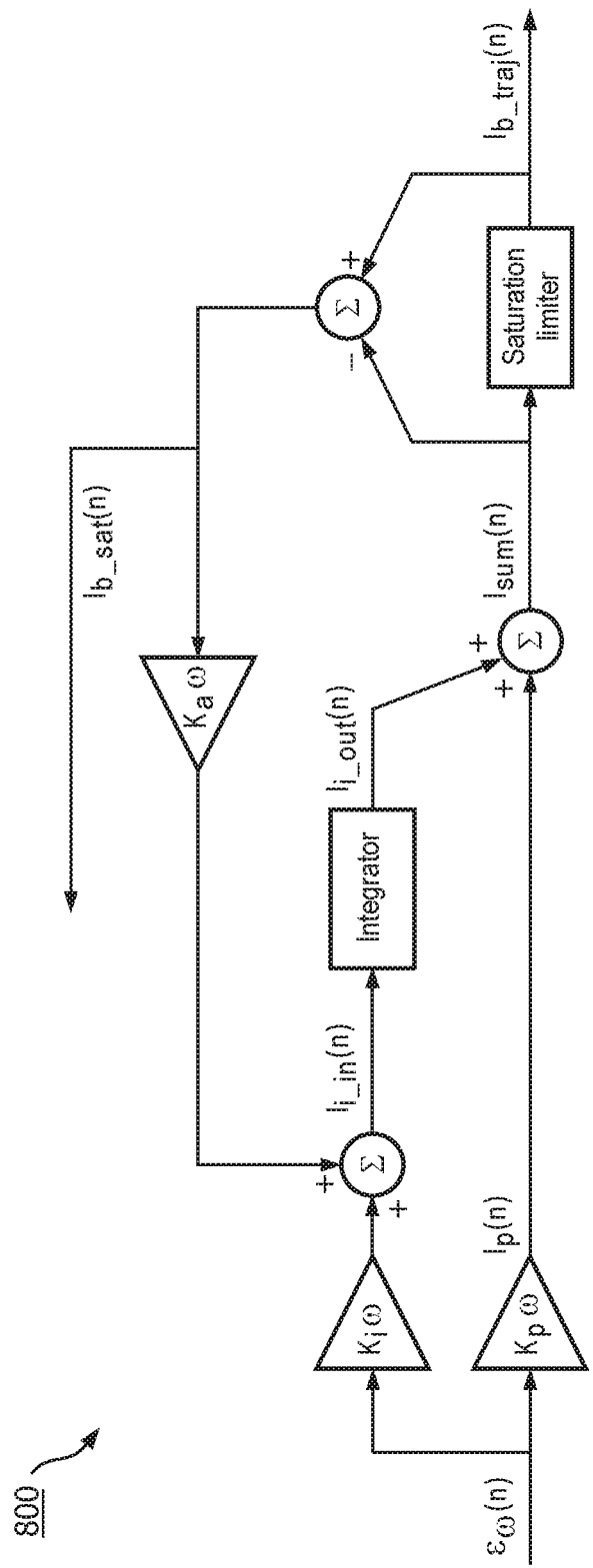
FIG. 8 is a schematic representation of a model for a non-invasive ventilator blower speed loop compensator, in accordance with an embodiment.

Referring to FIG. 8, in one embodiment, is a block diagram of a blower speed compensator 800. According to an embodiment, the speed error, $\varepsilon_\omega(n)$, is calculated as the difference between the speed trajectory, $\omega_{traj}(n)$ and the filtered speed estimate, $\hat{\omega}_f(n)$:

$$\varepsilon_\omega(n) = \omega_{traj}(n) - \hat{\omega}_f(n) \qquad \text{(Eq. 15)}$$

The filtered speed estimate can be obtained by filtering the raw speed estimate, $\hat{\omega}(n)$ with a $2^{nd}$ order low pass filter calculation and by using the following signal substitutions and parameter values: $x(n)=\hat{\omega}(n)$; $y(n)=\hat{\omega}_f(n)$; $\omega_o=1800$ rad/sec; $\zeta=0.707$; and $\Delta T=0.001$. Before describing how the raw speed estimate is determined, the blower speed compensator calculations are first described.

According to an embodiment, the blower speed compensator 800 is basically proportional integral control with fixed gains and anti-windup compensation, other mechanisms are possible. Typically the integral gain determines the speed (aka stiffness) in the control and the proportional gain adds damping and helps reduce overshoot. The bandwidth of the blower (open loop) linear frequency response is relatively slow and so to reach flow/pressure trajectories at high pressures in fractions of a second depends heavily on allowing the blower speed to saturate. It can also be important that the speed control allow the blower to saturate at its maximum speed, and also include rapid recovery from saturation immediately when the servo error changes sign. Saturation difference detected in the speed controller, $I_{b\_sat}(n)$, can also be transmitted back to the outer pressure loop in the controller cascade to assist the pressure controller integrator in dumping error during blower saturation.

The integrator input, $I_{i\_in}(n)$, is calculated as the sum of the scaled speed error, $\varepsilon_\omega(n)$, and scaled saturation difference:

$$I_{i\_in}(n) = K_{i\omega}\varepsilon_\omega(n) + K_{a\omega}I_{b\_sat}(n) \qquad \text{(Eq. 16)}$$

$$I_{b\_sat}(n) = I_{b\_traj}(n) - I_{sum}(n) \qquad \text{(Eq. 17)}$$

The proportional component of the current control, $I_p(n)$, can be calculated as the product of the speed compensator proportional gain, $K_{p\omega}$, and the speed control servo error:

$$I_p(n) = K_{p\omega}\varepsilon_\omega(n) \qquad \text{(Eq. 18)}$$

The integration is approximated in discrete time by a forward difference. The integrator output, $I_{i\_out}(n)$ can be calculated as:

$$I_{i\_out}(n) = \Delta T I_{i\_in}(n-1) + I_{i\_out}(n-1) \qquad \text{(Eq. 19)}$$

where the initial conditions are $I_{i\_in}(0)=0$ and $I_{i\_out}(0)=8192$. The unlimited control, $I_{sum}(n)$ is just the sum of the integral and proportional control components:

$$I_{sum}(n) = I_{i\_out}(n) + I_p(n) \qquad \text{(Eq. 20)}$$

The output of the speed control, the blower motor current trajectory, $I_{b\_traj}(n)$, can then be calculated as the control, constrained by the current limits:

$$I_{b\_traj}(n) = \min\{I_{b\_targMax}, \max\{I_{b\_targMinFilt}(n), I_{sum}(n)\}\} \qquad \text{(Eq. 21)}$$

$$\text{where } I_{b_{targMax}}(n) = \begin{cases} 8192 \text{ counts if } \mathfrak{I}_{targMin}(n) = 1 \\ 2000 \text{ counts if } \mathfrak{I}_{targMin}(n) = 0 \end{cases}, \text{ and}$$

$$I_{b\_targMin} = \text{Round}\left[2^{13}\left(1 - \frac{6.046 \text{ Amperes}}{8.0 \text{ Amperes}}\right)\right] = 14383 \text{ counts.}$$

According to an embodiment, $\mathfrak{I}_{targMin}(n)$ is initialized to zero, $\mathfrak{I}_{targMin}(n)$ is latched to 1 if the phase is exhalation and $\hat{\omega}(n) \leq 10000$ rpm, and $\mathfrak{I}_{targMin}(n)$ is reset to zero at the start of inhalation. According to an embodiment, $I_{b_{targMinFilt}}(n)$ is calculated using the generalized filter configured as a first order lag and using the following substitutions: $x(n)=I_{b\_targMin}(n)$, $y(n)=I_{b\_targMinFilt}(n)$, $a=0$, $b=1$, $c=\tau_{SpeedSwitch}=0.02$ sec, $d=1$, $\Delta T=0.001$, $y(0)=2000$ counts, and:

$$K_{p\omega} = 2.8239 \frac{\text{counts}}{\text{rpm}} \text{ and } K_{i\omega} = 48.2 \frac{\text{counts}}{\text{rpm} - \text{sec}} \text{ and}$$

$$K_{a\omega} = 1000/\text{sec.}$$

According to an embodiment, the filtered switching of the lower current bound allows the speed to approach lower values during the first part of exhalation, and thus lower resistance and work of breathing.

Blower Speed Estimator

From a modeling perspective, the three phase brushless motor can look similar to a DC motor exhibiting a linear relationship between current and torque, as well as voltage and rpm. Therefore the DC motor model can serve as an accurate estimator for speed. Accordingly, a discrete time estimator calculating the speed estimate $\hat{\omega}(k)$, can be derived in units of rpm by including the scale factor $30/\pi$:

$$\hat{\omega}(n) = \begin{cases} \frac{30}{\pi K_T}\left(V_m(n) - RI_m(n) - L\frac{I_m(n) - I_m(n-1)}{\Delta T}\right) & \text{for } \omega_{targ}(n-1) < 5000 \text{ krpm} \\ \omega_{tach}(n) & \text{otherwise} \end{cases} \quad \text{(Eq. 22)}$$

where the calculation constants are: R=0.21 Ohms; L=0.000045 Henries; $K_T$=0.0065 N-m/A; and $I_m(0)$ is initialized as zero.

Non-Invasive Ventilation $O_2$ Mix Controller

Figure 9:
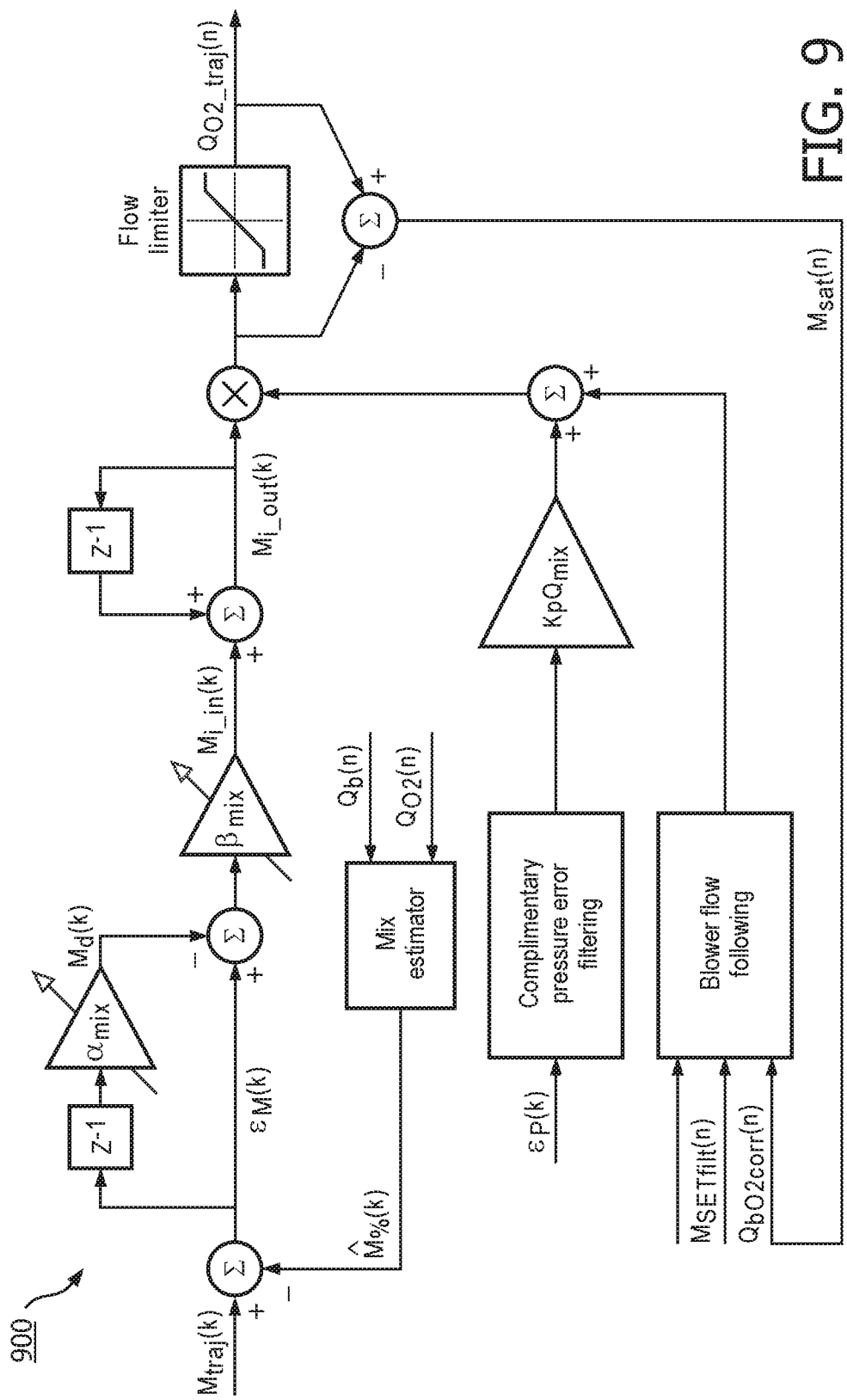
FIG. 9 is a schematic representation of a non-invasive ventilator mix controller, in accordance with an embodiment.

For invasive ventilation, control of the delivered gas oxygen concentration (mix) is typically managed by a simple ratiometric division of the total flow target. This applies to either volume-cycled ventilation or pressure-cycled ventilation, and since the $O_2$ and air valves are typically matched, or rather close enough in terms of their static sensitivity and dynamic response, correction of the mix is usually not required to meet specified accuracy. The use of flow feedback controls for air & $O_2$, which further improve the accuracy of the flow controls, reinforces this assumption. But for some non-invasive ventilation mix control, there can be a dynamic mismatch between the blower and the $O_2$ valve flow response. The mismatch, not to mention output mixed gas returning to the blower flow pathway, makes the ratiometric approach difficult if not impossible to realize, causing pressure control instabilities and large mix errors. To manage mix control, a different approach can be used where the $O_2$ flow servo follows the total flow response. As noted above, this is called "slaving" or "slave control." For this architecture a positive feedback loop occurs relative to the $O_2$ flow measurement. Stability is only possible since, for the overall pressure control system (which contains mix controls) the negative pressure feedback loop remains dominant. The slaving approach provides fairly consistent pressure response and suitable mix accuracy over the full range of settings and expected patient loads. FIG. 9 only illustrates the general structure 900 of the controller components for this approach, as well as the connections between them. More complete details of this approach are provided below.

For mix control some calculations proceed over the regular control interval $\Delta T$, and these calculations are indexed by the variable n=1, 2, 3 . . . . Other calculations are updated only once per breath cycle either at the start of inhalation or the start of exhalation. These calculations have a variable time interval (depending on the set breath rate or trigger intervals) and are indexed by the variable k=1, 2, 3 . . . .

The breath to breath control of mix sets an inherent sampling rate fixed by either the set breath rate or in the case of patient triggered breaths, a measured rate that varies according to the last breath interval. According to Shannon's sampling theorem one cannot expect to recover and utilize information if sampling occurs any slower than half the highest frequency expected to be controlled. As the breath rate changes, so must the controller structure to maintain stable closed loop control with consistent transient response. This creates an issue in the time the system can respond to a change in setpoint for feedback alone, and so a feedforward component is also required with gain <1.0 to get the mix control moving immediately in the right direction. The slower response of closed loop control then follows.

According to an embodiment, the closed loop mix control is derived by the method of pole placement; a method of direct synthesis where the desired closed loop system dynamics are assumed as the design goal—in terms of its closed loop poles. In this design approach the continuous time (mix) system is assumed to be a first order response with time constant of 10 sec. A zero order hold is assumed, and the combination of these two elements is transformed to an equivalent discrete time system. The discrete time plant and the desired closed loop system are then used to calculate the structure and gains for the controller.

Mix Correction

Mix correction can be performed, for example, using feedback control based on a mix estimator rather than any means of direct measurement of oxygen concentration. The estimation uses blower and flow measurements as well as flow path assumptions. Corrections are updated on a breath by breath basis and are applied as a factor that reduces the oxygen flow component. Mix correction is generally needed to manage the issue of rebreathing but it can also correct for dynamic differences between the blower and compressed oxygen valve gas deliveries. The Mix correction controller calculates a mix correction factor at the start of every breath. The greater the influence of rebreathed oxygen, the smaller the factor will be. A factor near 1 indicates little or no rebreathing.

Mix correction can begin first by computing the mix error, $\varepsilon_M(k)$, for each breath, determined by the difference of the mix trajectory, $M_{tarj}(k)$, and the estimated percent mix, $\hat{M}_{\%}(k)$:

$$\varepsilon_M(k) = M_{tarj}(k) - \hat{M}_{\%}(k) \quad \text{(Eq. 23)}$$

According to an embodiment, UserMixSetting(n) is the value of mix set by the user, updated at $\Delta T$ sec:

$$M_{SET}(n) = \begin{cases} \min\{99, UserMixSetting(n)\} & \text{only if phase is exhalation} \\ M_{SET}(n-1) & \text{otherwise} \\ M_{SET}(0) = 21.0 \end{cases} \quad \text{(Eq. 24)}$$

$$M_{traj}(k) = \begin{cases} M_{SET}(n) & \text{only at the start of inhalation} \\ M_{traj}(k-1) & \text{otherwise} \\ M_{traj}(0) = 21.0 \end{cases} \quad \text{(Eq. 25)}$$

According to an embodiment, a filter can be utilized to create a smooth trajectory for the input to the blower flow following filter. $M_{SETfilt}(n)$ can be calculated by substituting the following: $x(n) = M_{SET}(n)$, $y(n) = M_{SETfilt}(n)$, a=0, b=1, c=0.1 sec, d=1, $\Delta T$=0.001 sec, and y(0)=21.0.

The mix compensator integrator input, $M_{i\_in}(k)$, is calculated as:

$$M_{i\_in}(k) = \beta_{mix}(k)[\varepsilon_M(k) - \alpha_{mix}(k)\varepsilon_M(k-1)] \quad \text{(Eq. 26)}$$

where $\varepsilon_M(0) = 0.0$. To maintain consistent sample-response, independent of the breath rate setting, the $\alpha\beta$ and gains are calculated on a breath to breath basis, derived directly from the synthesis as the poles and zeros are expressed in exponential form:

$$\alpha_{mix}(k) = e^{-\frac{T_B(k-1)}{\tau_{mix}}} \quad \text{(Eq. 27)}$$

$$\beta_{mix}(k) = 20.0\tau_{mix}(1 - \alpha_{mix}(k)) \quad \text{(Eq. 28)}$$

where $T_B(k)$ is the breath interval in seconds, $T_B(0) = 1.0$, and $-\tau_{mix} = 2$ sec.

According to an embodiment, the integration output is calculated by a simple backward difference, however clamped by the minimum and maximum correction factors as $$M_{i_{out}}(k) = \begin{cases} \max\{0.3, \min\{0.97, (M_{i\_in}(k) + M_{i\_out}(k-1))\}\} & \text{for } M_{reset}(n) \neq 1 \\ 0.5 & \text{for } M_{reset}(n) = 1 \end{cases} \quad \text{(Eq. 29)}$$

where the initial conditions are $M_{i_{out}}(0)=0.5$.

For anti-windup of the blower flow following filter, the mix difference, $M_{sat}(n)$ is calculated as:

$$M_{sat}(n) = Q_{O2traj}(n) - M_{i_{out}}(n) Q_{O2ref}(n) \quad \text{(Eq. 30)}$$

According to an embodiment, the controller is reset under two conditions: (1) the set mix is 21%—(in this case the controller is held in reset for all breaths as long as the set mix is 21%) or (2) there was a change in the mix trajectory (and in this case the controller is only reset to its reset value for that one breath):

$$M_{reset}(n) = \{M_{traj}(k) \neq M_{traj}(k-1)\} \text{ OR } \{M_{set}(n) = 21\%\} \quad \text{(Eq. 31)}$$

where $M_{traj}(0)=21$.

The sequential logic related to user mix setting changes, what they affect immediately, and how specific changes are constrained by breath states or events are correctly specified by the logic statements herein. Immediate changes in mix can only happen during exhalation and are acted on by the BFF and CPC filter components. But the actions of the closed loop mix controller are more delayed, only initiated at the start of the breath, and further constrained by reset conditions.

After the oxygen reference flow is calculated, the corrected mix factor can be applied to calculate the oxygen flow servo trajectory from the total filtered flow rate at standard control rate (every 1 ms):

$$Q_{O2\_traj}(n) = \min\{Q_{O2max}, \max\{0, M_{i\_out}(k) * Q_{O2ref}(n)\}\} \quad \text{(Eq. 32)}$$

$Q_{O2ref}(n)$ is comprised of two components, the filtered blower flow following component, $Q_{O2refB}(n)$ and the complimentary filtered pressure error component, $Q_{O2refP}(n)$:

$$Q_{O2ref}(n) = Q_{O2refB}(n) + K_{PQmix} Q_{O2refP}(n) \quad \text{(Eq. 33)}$$

where $K_{PQmix}=4.0$

For each filtered component, a scale factor, $K_f(n)$, and filter pole, $\alpha_f(n)$ are calculated at each time step:

$$\alpha_f(n) = \frac{100 - M_{SETfilt}(n)}{79\tau_{PQ}} \quad \text{(Eq. 34)}$$

$$K_f(n) = \frac{M_{SETfilt}(n) - 21}{79\tau_{PQ}} \quad \text{(Eq. 35)}$$

where $\tau_{PQ}=0.02$. According to an embodiment, $\tau_{PQ}$ is an adjusting factor that, for high mix setting trades off the tracking stiffness and noise coupling between the blower and oxygen flows. A small $\tau_{PQ}$ provides stiff tracking however noisier oxygen flow.

According to an embodiment, the filtered blower flow component is calculated using a low pass filter acting on the mix corrected blower flow measurement $$Q_{O2refB}(n) = K_f(n) y(n) \quad \text{(Eq. 36)}$$

$$y(n) = \Delta T[K_{af}M_{sat}(n-1) + Q_{bO2corr}(n-1)] + (1 - \Delta T\alpha_f(n-1))y(n-1) \quad \text{(Eq. 37)}$$

where $K_{af}=1.0$, $M_{sat}(0)=0.0$, $\alpha_f(0)=0.0$, $Q_{bO2corr}(0)=0.0$, and $y(0)=0.0$.

According to an embodiment, the complimentary filtered pressure error component is calculated as a high pass filter in series with a low pass filter (net effect: bandpass) acting on the pressure error:

$$Q_{O2refP}(n) = [1 - \Delta T\alpha_f(n-1)]Q_{O2refP}(n-1) + \Delta T\alpha_f(n-1)y(n-1) \quad \text{(Eq. 38)}$$

$$y(n) = \frac{K_f(n)}{\alpha_f(n)}[\varepsilon_P(n) - \alpha_f(n)z(n)] \quad \text{(Eq. 39)}$$

$$z(n) = \Delta T\varepsilon_P(n-1) + [1 - \Delta T\alpha_f(n-1)]z(n-1) \quad \text{(Eq. 40)}$$

where, $\varepsilon_p(0)=0.0$, $y(0)=0.0$, $z(n)=0.0$, and $Q_{O2refP}(0)=0.0$.

Mix Estimator

According to an embodiment, the mix estimator can be used to provide a feedback estimate for the $O_2$ correction part of the mix controller. The goals behind the mix estimator design are, for example: (1) provide an average estimate of delivered mix over multiple breaths; (2) model the reverse flow behavior and correct the estimate for the $O_2$ enriched air at the start of breaths. The instantaneous oxygen concentration (mix) in the simplest form (assuming no reverse metabolic products or mixed gas from prior breaths) can be determined by the ratio of the oxygen fraction of the flow to the total gas flow.

Referring to FIG. 10, in one embodiment, is a schematic representation of a mix controller mix estimator 1000. The blower mix factor, $K_{b\_O2}(n)$, can be selected according to the state of the rebreathing window, $W_R(n)$:

$$K_{b\_O2}(n) = \begin{cases} 0.21 & \text{for } W_R(n) \text{ false} \\ \hat{M}_E(k) & \text{otherwise} \end{cases} \quad \text{(Eq. 41)}$$

where $\hat{M}_E(k)$ is the sampled instantaneous estimated mix fraction (sampled on the falling edge of e(n). $W_R(n)$ is a window, which when true indicates enriched air is contained within the blower pathway. $W_R(n)$ is also called the "rebreathing window" which is updated on the control cycle and is defined further below by the state chart diagrams. When $W_R(n)$ is true, it indicates that $O_2$ enriched air from the previous breath remains in the blower pathway, and that the last sampled instantaneous estimated mix fraction should be used to determine the oxygen fraction of blower supplied gas. When $W_R(n)$ is cleared, blower supplied gas is assumed to be at 21%.

FIG. 10 illustrates, for example, that there are three separate averages that can be continuously maintained: (i) the averaged total blower flow, $\overline{Q}_{bT}(n)$; (ii) the averaged effective oxygen flow from the $O_2$ valve, $\overline{Q}_{O2}(n)$; and (iii) the averaged fraction of blower flow that is pure $O_2$, $\overline{Q}_{bO2}(n)$.

According to an embodiment, since the blower flow sensor is always set to measure air, $Q_b(n)$ is corrected for expected gas composition according to the user set mix, $M_{set}(n)$ as $Q_{bO2corr}(n)$ and $Q_{bO2corr}(n)$ is limited to positive flow since positive flow is what the estimator is concerned with. Note also that $K_{b\_O2}(n)$ is latched from the instantaneous mix estimate, $\hat{M}(n)$, and on the falling edge of e(n). These particular signals and the timing are critical to provide accurate mix estimate for high breath rate, moderate to high volume, high set mix conditions where rebreathing effects become significant.

To estimate the averages, the mix estimator can use special $1^{st}$ order lag (filters) that provide latching capability according to the blower state. According to an embodiment, three instances are required where the following substitution of variables and parameters are applied, and the enable logic for each of the three filters is determined by the direction of flow in the manifold. Mix is only estimated for flow moving toward the patient. Negative flow is not admitted to the filters $e(n)=(Q_{blower}(n)>0)$.

First, the blower and oxygen flows are corrected. The blower flow is corrected for the current mix in the blower flow sensor:

$$Q_{bO2corr}(n) = \left[1 - \left(\frac{M_{SET}(n) - 21}{79}\right)\left(0.0442 - \frac{2.21}{50 + |Q_b(n)|}\right)\right]Q_b(n) \quad \text{(Eq. 42)}$$

And the oxygen flow is clipped to zero:

$$Q_{O2corr}(n) = \max\{0, Q_{O2}(n)\} \quad \text{(Eq. 43)}$$

The net flow is the sum of blower and oxygen flow. The physical difference between blower and compressed gas flow is that the blower can sink flow as well as source it. The compressed oxygen gas can only source flow. During breath delivery the composition and size of the gas stream going to the patient, $Q_{net}$, will be affected by the direction of the blower flow, $Q_b$, and the size of the flow relative to the size of oxygen flow, $Q_{O2}$. These conditions define a distinct flow state that can be used as a basis for estimating more accurate mix. For example, a first and second flow state can define net flow going towards the patient. A third flow state can define exhalation. In flow state 1, both blower and oxygen gases flow towards the patient. In flow state 2, the blower flow is reversed, but because the blower flow is less than the oxygen flow, the net flow is the difference, and is composed of pure oxygen. Flow state 4 accounts for the case where the blower flow is equal and opposite the oxygen flow; oxygen gas is all flowing out of the blower, and the net flow to the patient is zero. The set of mutually exclusive manifold states are as follows:

For $Q_{bO2corr}(n) \geq 0$, FlowState($n$)=1

For $Q_{bO2corr}(n)<0$ AND $Q_{O2corr}(n)>-Q_{bO2corr}(n)$, FlowState($n$)=2

For $Q_{bO2corr}(n)<0$ AND $Q_{O2corr}(n)<-Q_{bO2corr}(n)$, FlowState($n$)=3

For $Q_{bO2corr}(n)<0$ AND $Q_{O2corr}(n)==-Q_{bO2corr}(n)$, FlowState($n$)=4 (Eq. 44)

The estimator filter enable, e(n) becomes:

$$e(n) = (\{FlowState(n)==1\} \text{ OR } \{FlowState==2\}) \quad \text{(Eq. 45)}$$

where the following define the other inputs and outputs of the three filters in the mix estimator:

$$\alpha = 0.004 \text{ and } \tau_M = \frac{\Delta T * (1 - \alpha)}{\alpha}.$$

(1) For $\overline{Q}_{bO2}(n)$, the Oxygen Component of Blower Flow:
$x(n) = K_{b\_O2}(n) \max\{0, Q_{bO2corr}(n)\}$; $y(n) = \overline{Q}_{bO2}(n)$; $\tau = \tau_M$; $\Delta T = 0.001$ seconds; and $y_o = 0.21$ (assumes air is initially in the circuit).

(2) For $\overline{Q}_{bT}(n)$, the Total Blower Flow:
$x(n) = \max\{0, Q_{bO2corr}(n)\}$; $y(n) = \overline{Q}_{bT}(n)$; $\tau = \tau_M$; $\Delta T = 0.001$ seconds; and $y_o = 1.0$ (the initial condition for this filter avoids the divide by zero at start up).

(3) For $\hat{Q}_{O2}(n)$, the Flow from the Compressed Oxygen Gas Valve:

$$x(n) = \quad \text{(Eq. 46)}$$
$$Q_{O2effective}(n) \begin{cases} 0 & \text{if } FlowState(n) = 3 \\ Q_{bO2corr}(n) + Q_{O2}(n) & \text{if } FlowState(n) = 2 \\ Q_{O2}(n) & \text{otherwise} \end{cases}$$

$$y(n) = \overline{Q}_{O2}(n)$$

where $\tau = \tau_M$; $\Delta T = 0.001$ seconds; and $y_o = 0.0$.

At each control step n, the instantaneous mix fraction estimate, $\hat{M}(n)$, can be calculated as:

$$\hat{M}(n) = \max\left\{0.21, \min\left\{1.00, \left(\frac{\overline{Q}_{bO2}(n) + \overline{Q}_{O2}(n)}{\overline{Q}_{bT}(n) + \overline{Q}_{O2}(n)}\right)\right\}\right\} \quad \text{(Eq. 47)}$$

At the start of each inspiration, the breath averaged mix fraction of the estimate, $\overline{M}(n)$, can be sampled providing the mean value of $\overline{M}(n)$ over the last breath:

$$\overline{M}(k) = \frac{\sum_{n \text{ at the start of breath}(k-1)}^{n \text{ at the end of breath}(k-1)} \hat{M}(n)}{\text{Number of samples in breath}(k-1)} \quad \text{(Eq. 48)}$$

and the percent mix estimate, $\overline{M}_\%(k)$, calculated for use in the mix controller:

$$\hat{M}(k) = \begin{cases} \overline{M}(k) & \text{at the start of inhalation} \\ \hat{M}(k-1) & \text{otherwise} \end{cases} \quad \text{(Eq. 49)}$$

$$\hat{M}_\%(k) = 100\hat{M}(k) \quad \text{(Eq. 50)}$$

To complete the mix estimator, the estimated mix fraction from the prior delivered breath, $\overline{M}_E(n)$, can be sampled when the net flow goes negative:

$$\hat{M}_E(k) = \begin{cases} \hat{M}(n) & \text{on the falling edge of } e(k) \\ \hat{M}_E(k-1) & \text{otherwise} \end{cases} \quad \text{(Eq. 51)}$$

Rebreathing Window State Logic

Figure 11:
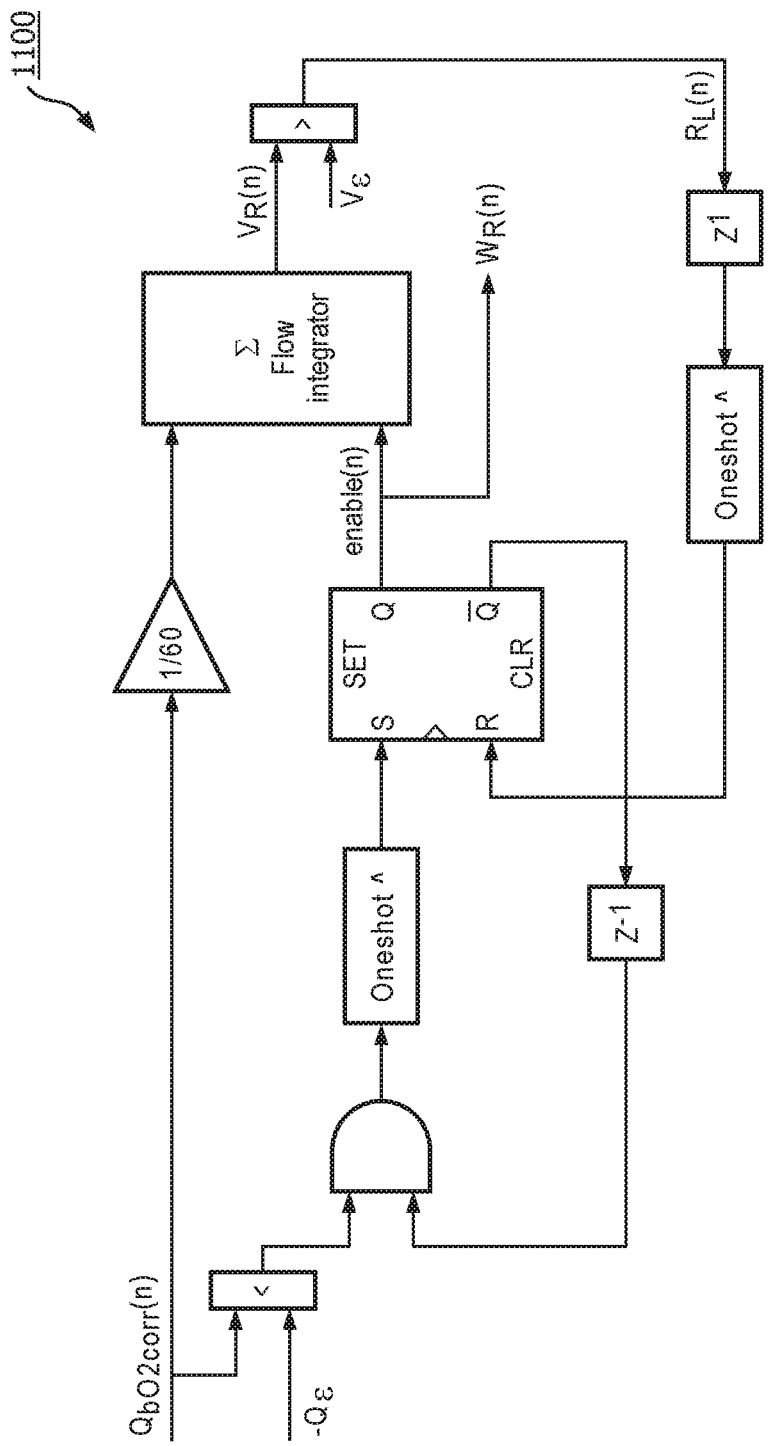
FIG. 11 is a schematic representation of rebreathing sequential logic, in accordance with an embodiment.

Referring to FIG. 11, in one embodiment, is a block diagram showing rebreathing sequential logic 1100. The Rebreathing Logic determines the state of the Rebreathing Window, $W_R(n)$ which, when TRUE, indicates that some portion of oxygen enriched gas from a prior breath has entered the blower limb of the manifold during exhalation. It thus provides an indicating signal to the mix estimator for enriching the $O_2$ concentration of blower inlet gas during either restoration of bias flow during exhalation or at the start of inhalation on the subsequent breath. The logic detects and calculates the volume of this enriched gas and applies such (up to the assumed dead space limitation) to activate the signal.

Note that the rebreathing window timing is independent of the IE signal and depends only on the zero crossings of blower flow. This is an essential design feature since at high breath rate, there is significant phase shift between the IE and $Q_b$ signals:

$$V_R(n) = 1000[\max\{\min\{V_\Sigma(n), V_{Rmax}\}, V_{Rmin}\}] \quad \text{(Eq. 52)}$$

$$V_\Sigma(n) = \begin{cases} \dfrac{Q_{bO2corr}(n)}{60}\Delta T + V_1(n-1) & \text{when reset is clear} \\ V_1(n-1) & \text{when reset is set} \end{cases} \quad \text{(Eq. 53)}$$

$$V_1(n) = \begin{cases} 0.001 V_R(n) & \text{when reset is clear} \\ 0 & \text{when reset is set} \end{cases} \quad \text{(Eq. 54)}$$

$$V_{Rmax} = \dfrac{V_D}{1000} \quad \text{(Eq. 55)}$$

$$V_{Rmin} = -V_{Rmax} \quad \text{(Eq. 56)}$$

$$\text{reset}(n) = \dfrac{V_D = 155 \text{ mL}}{\text{enable}(n)} \quad \text{(Eq. 57)}$$

$$\text{enable}(n) = \mathbb{Q} \text{ output of } SR_{FlipFlop(n)} \quad \text{(Eq. 58)}$$

The SR_FlipFlop function operates in the same manner as a digital set-reset flip flop or latch. $\mathbb{S}(n)$ is the 'set' input and $\mathbb{R}(n)$ the reset input with C in the table representing the (rising) edge of the clock which is coincident with the increment of n. The flip flop inputs are defined as follows.

$$\mathbb{S}(n) = \begin{cases} 1 & \text{on the rising edge of } \{[Q_{BO2corr}(n) < -Q_\varepsilon] \text{ AND } \overline{\mathbb{Q}}(n-1)\} \\ 0 & \text{otherwise} \end{cases} \quad \text{(Eq. 59)}$$

$$\mathbb{R}(n) = \begin{cases} 1 & \text{on the rising edge of } R_L(n-1) \\ 0 & \text{otherwise} \end{cases} \quad \text{(Eq. 60)}$$

$$R_L(n) = \text{StartOfExhalation OR } V_R(n) > V_\varepsilon \quad \text{(Eq. 61)}$$

where $V_\varepsilon$=1 mL, $Q_\varepsilon$=1 lpm:

$$W_R(n) = \text{enable}(n) = \mathbb{Q}(n) \quad \text{(Eq. 62)}$$

For $Q_{bO2corr}(n)$, as defined earlier, this is the mix-corrected, measured blower sensor flow in lpm. Positive flow moves from the blower towards the safety valve and patient port. $V_D$ is the effective deadspace volume.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

What is claimed is:

1. A ventilator configured to control a pressure and gas mixture for an air flow, the ventilator comprising:
    a gas source;
    a proportional valve configured to control a gas flow rate from the gas source;
    a mix controller in communication with the proportional valve, wherein the mix controller is configured to monitor a flow of gas through a blower, and further configured to control a percentage of oxygen in output flow;
    a blower motor; and
    a blower motor controller configured to control a speed of the blower motor using a blower speed feedback loop configured to generate a speed output signal, a flow feedback loop, and a pressure feedback loop, wherein the blower motor controller comprises a complimentary filter configured to blend a machine pressure signal at a first frequency and a proximal pressure signal at a second frequency, lower than the first frequency, into a single feedback signal, and wherein the pressure feedback loop is configured to receive as input: (i) a pressure trajectory; (ii) the single feedback signal from the complimentary filter; and (iii) the speed output signal from the blower speed feedback loop.

2. The ventilator of claim 1, wherein the mix controller and the blower controller are configured to cooperatively control the output flow.

3. The ventilator of claim 1, wherein the blower speed feedback loop is configured to provide linear control of the speed of the blower motor and maintain a speed limitation.

4. The ventilator of claim 1, wherein the flow feedback loop is configured to minimize a disturbance of air flow pressure in the ventilator.

5. The ventilator of claim 1, wherein the pressure feedback loop is configured to track an applied pressure trajectory.

6. The ventilator of claim 1, further comprising a speed controller, the speed controller configured to monitor the speed of the blower motor.

7. The ventilator of claim 1, further comprising a pseudo-derivative feedback compensator.

8. The ventilator of claim 1, wherein the flow feedback loop is configured to minimize a disturbance of blower gas flow pressure in the ventilator relative to a desired flow trajectory.

9. A method for controlling a pressure and gas mixture for an air flow of a ventilator, the method comprising the steps of:
    providing a ventilator, the ventilator comprising: a gas source; a proportional valve configured to control a gas flow rate from the gas source; a mix controller in communication with the proportional valve and a blower flow sensor; a blower motor; a blower motor controller comprising a complimentary filter configured to blend a machine pressure signal at a first frequency and a proximal pressure signal at a second frequency, lower than the first frequency, into a single feedback signal; and a pressure controller comprising a flow controller and a speed controller;
    activating the blower motor and opening the proportional valve to create flow pressure and mix in the ventilator;
    controlling, by the blower motor controller, the speed of the blower motor using a blower speed feedback loop configured to generate a speed output signal, a flow feedback loop, and a pressure feedback loop, wherein the pressure feedback loop is configured to receive as input: (i) a pressure trajectory; (ii) the single feedback signal from the complimentary filter; and (iii) the speed output signal from the blower speed feedback loop;
    monitoring, by the mix controller, a flow through the blower; and
    adjusting, using the mix controller, the proportional valve flow to provide mix control.

10. The method of claim 9, further comprising the steps of:
    monitoring, using a speed controller, a speed of the blower motor; and
    adjusting, using the speed controller, the speed of the blower motor.

* * * * *